United States Patent
Kent et al.

(10) Patent No.: US 7,090,636 B2
(45) Date of Patent: *Aug. 15, 2006

(54) PERMANENT MAGNET KEEPER-SHIELD ASSEMBLY

(75) Inventors: Thomas B. Kent, Boulder, CO (US); Robert K. Mitchiner, Longmont, CO (US); Caryn Peterson, Encinitas, CA (US); Scott Raymond Rudge, Boulder, CO (US); David Glover, Agua Dulce, CA (US)

(73) Assignee: Fe Rx Incorporated, San Diego, CA (US)

(*) Notice: Subject to any disclaimer, the term of this patent is extended or adjusted under 35 U.S.C. 154(b) by 90 days.

This patent is subject to a terminal disclaimer.

(21) Appl. No.: 10/734,651

(22) Filed: Dec. 12, 2003

(65) Prior Publication Data

US 2004/0181116 A1 Sep. 16, 2004

Related U.S. Application Data

(63) Continuation-in-part of application No. 10/087,442, filed on Mar. 1, 2002, now Pat. No. 6,663,555, which is a continuation of application No. 09/538,952, filed on Mar. 31, 2000, now Pat. No. 6,488,615.

(51) Int. Cl.
*A61N 2/00* (2006.01)

(52) U.S. Cl. .................................................... 600/9
(58) Field of Classification Search .......... 600/9–15; 424/490, 489, 464, 426, 450; 250/496.1, 250/497.1, 506.1, 515.1; 335/209, 214, 301, 335/302–305
See application file for complete search history.

(56) References Cited

U.S. PATENT DOCUMENTS

| 5,705,195 | A  | * | 1/1998  | Volkonsky et al. | ......... 424/490 |
| 6,200,547 | B1 | * | 3/2001  | Volkonsky et al. | ........ 424/9.36 |
| 6,488,615 | B1 | * | 12/2002 | Mitchiner et al. | ............. 600/9 |
| 6,663,555 | B1 | * | 12/2003 | Mitchiner et al. | ............. 600/9 |

* cited by examiner

*Primary Examiner*—John P. Lacyk
(74) *Attorney, Agent, or Firm*—The McCallum Law Firm, LLC.

(57) ABSTRACT

A magnet keeper-shield assembly adapted to hold and store a permanent magnet used to generate a high gradient magnetic field that, in one embodiment, may penetrate into deep targeted tumor sites in order to attract magnetically responsive micro-carriers. The magnet keeper-shield assembly includes a magnetically permeable keeper-shield with a bore dimensioned to hold the magnet. A lever mechanism is used to push the magnet partially out of the keeper-shield. The actuator is assisted by several springs extending through the base of the keeper-shield.

35 Claims, 22 Drawing Sheets

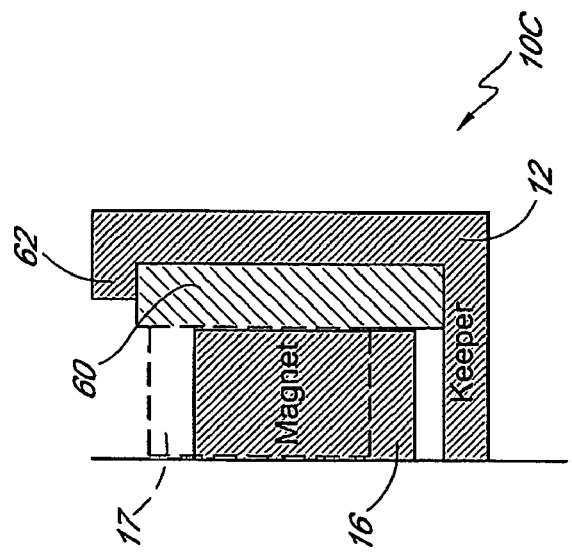
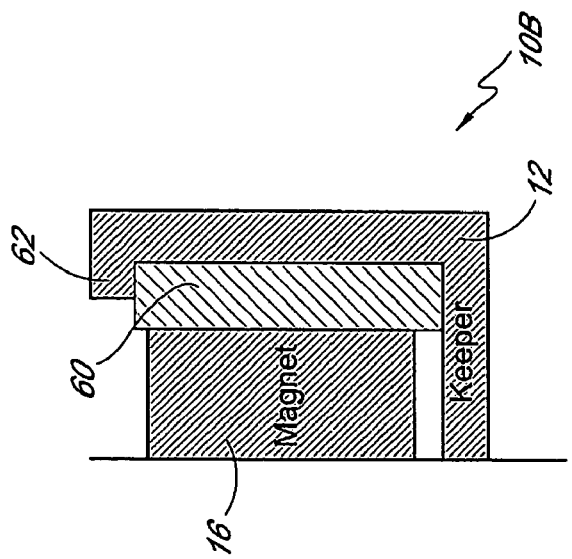
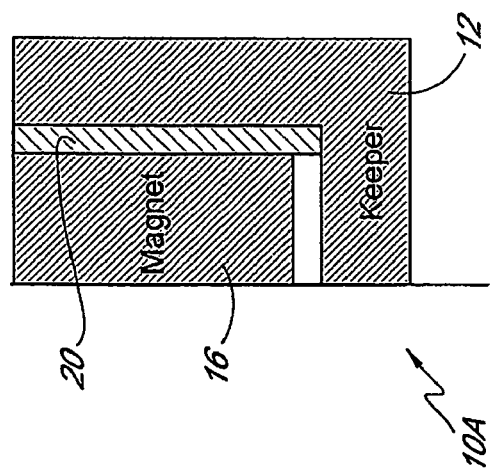
FIG. 12C
FIG. 12B
FIG. 12A

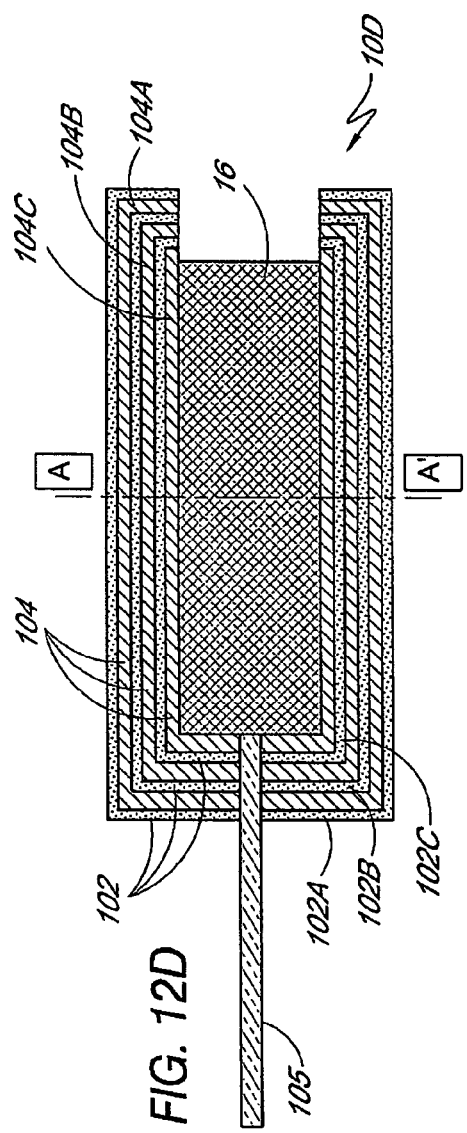
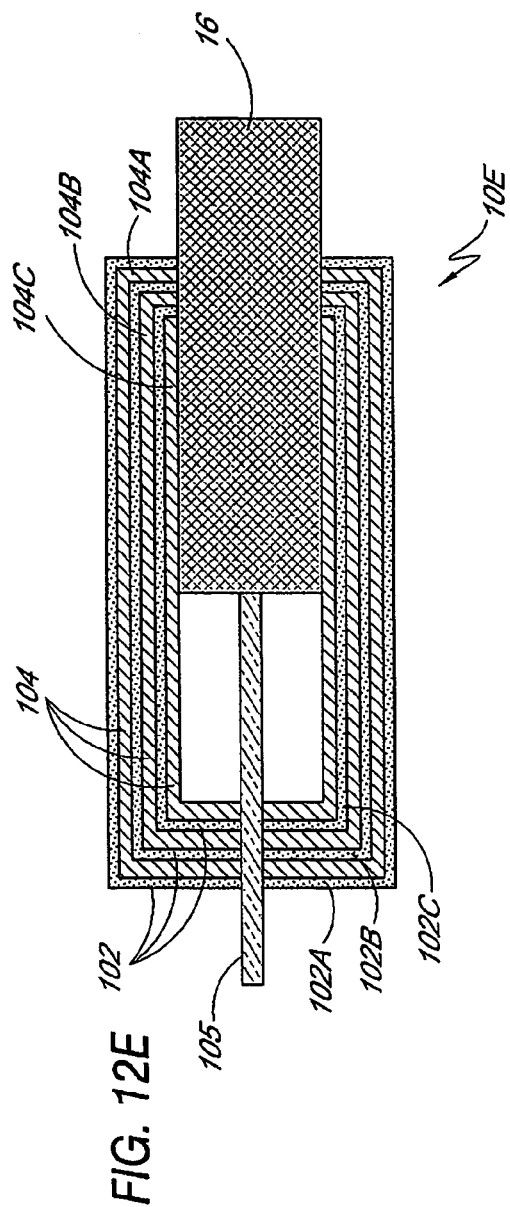
FIG. 12D
FIG. 12E

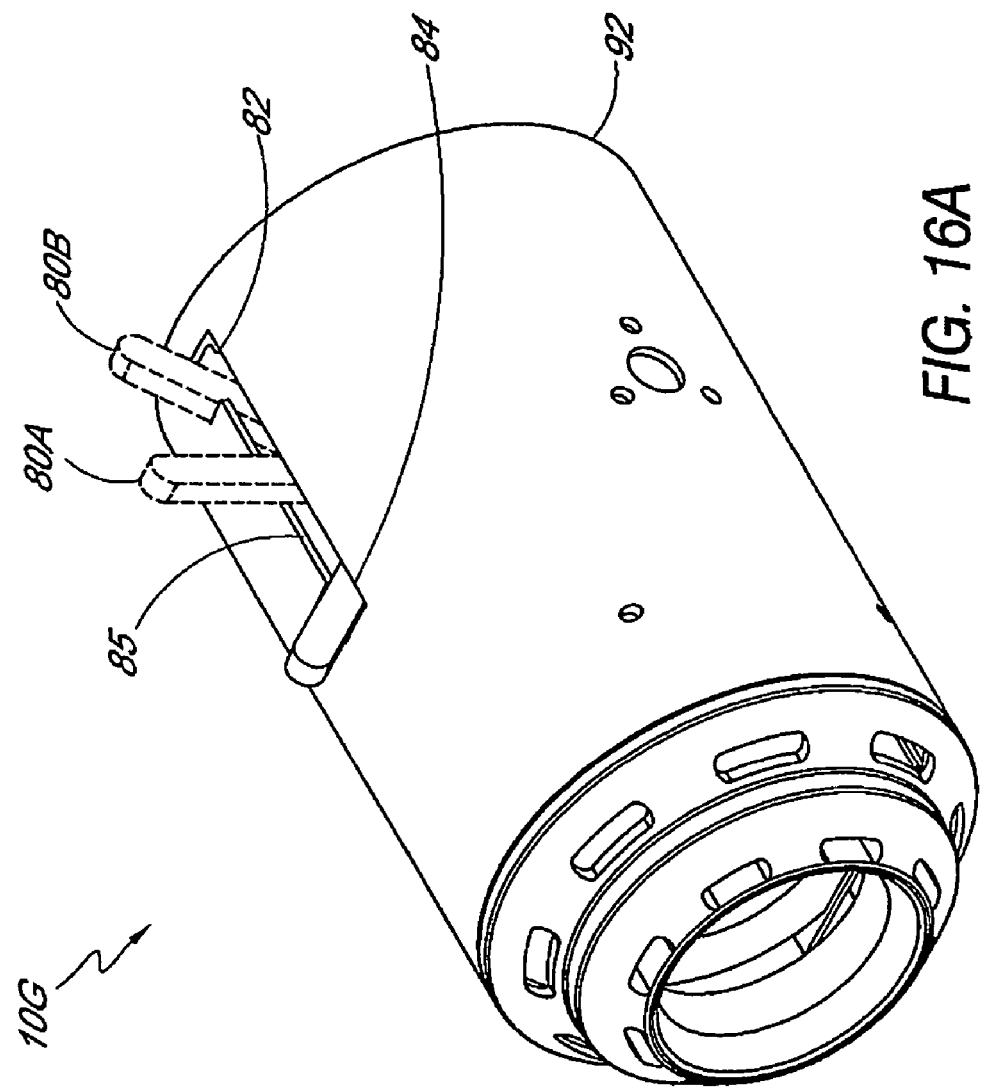

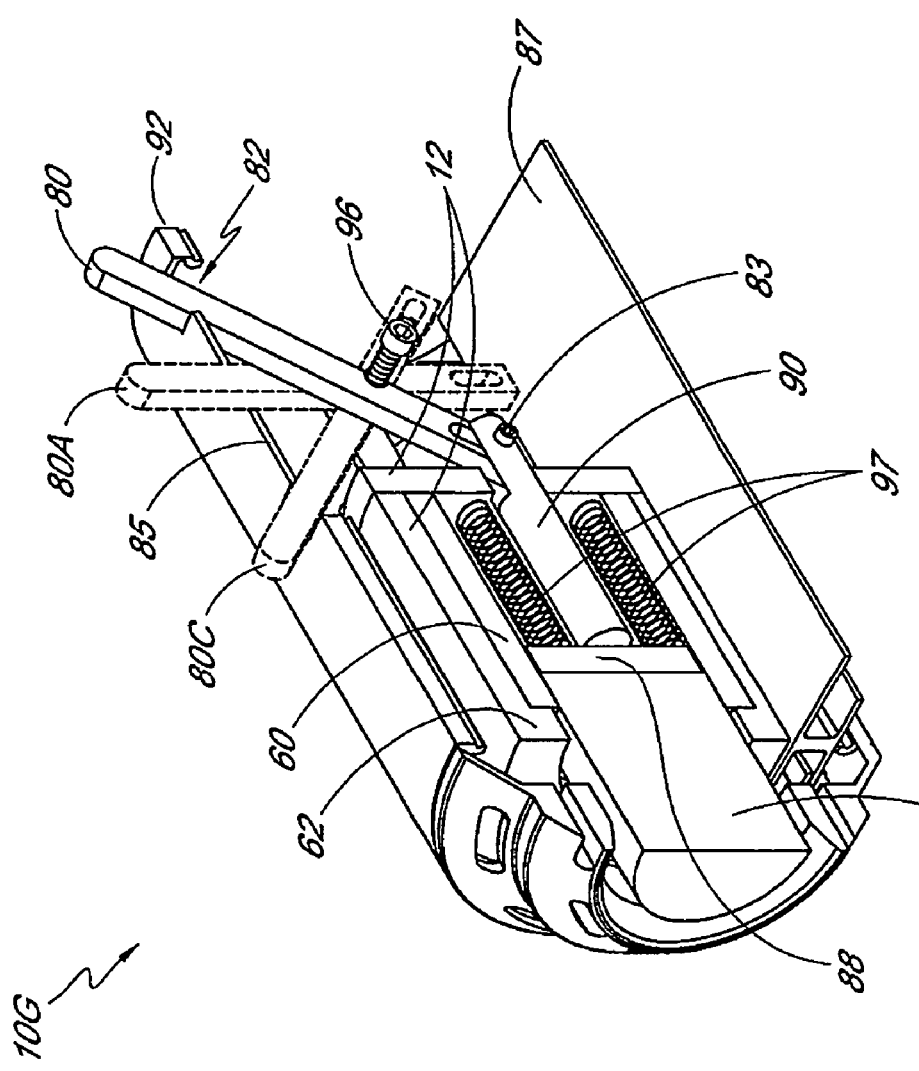

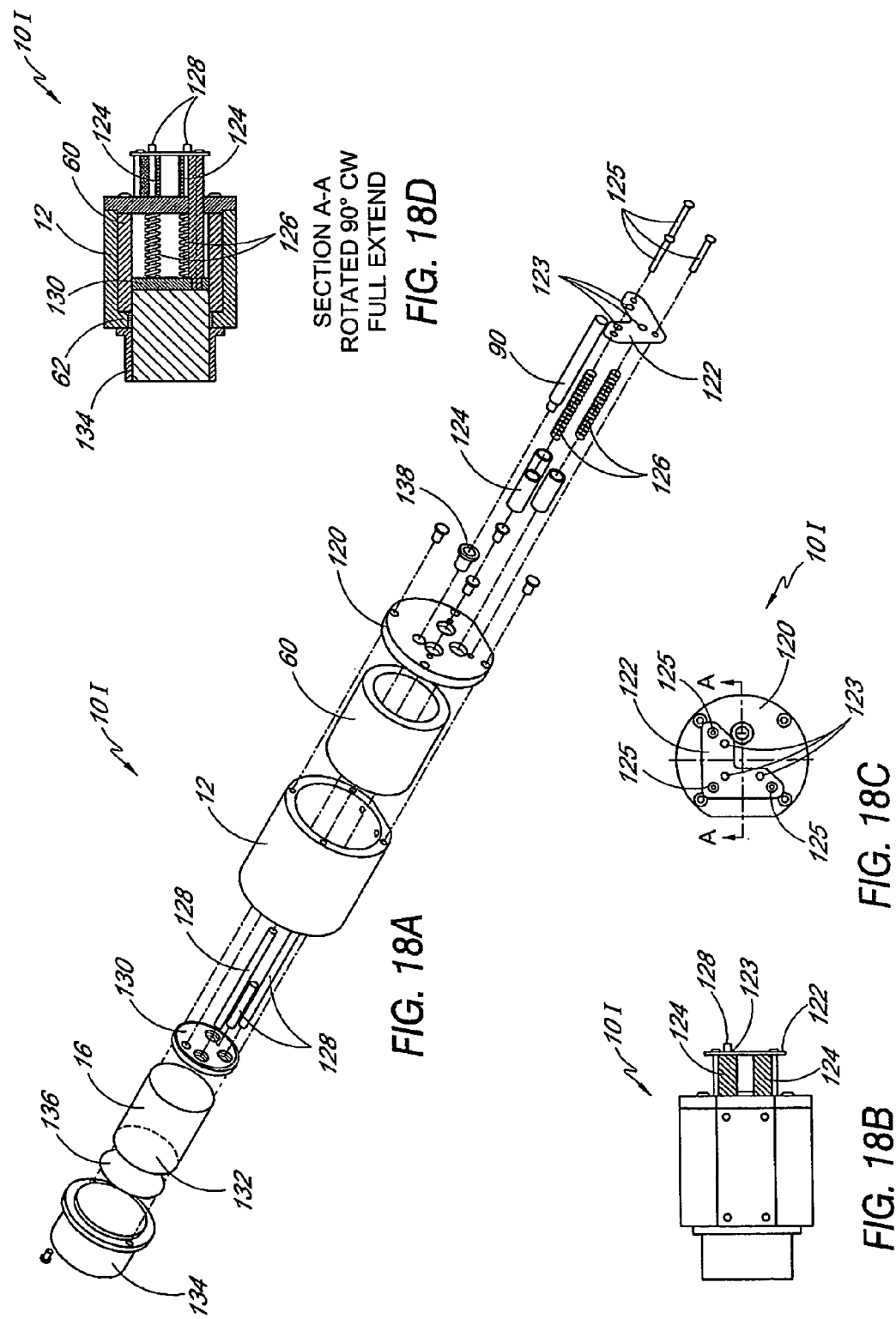

PERMANENT MAGNET KEEPER-SHIELD ASSEMBLY

CROSS REFERENCE TO RELATED APPLICATION

This application is a continuation in part of U.S. patent application Ser. No. 10/087,442, filed Mar. 1, 2002 now U.S. Pat. No. 6,663,555, which is a continuation of U.S. Pat. No. 6,488,615, filed on Mar. 31, 2000, both of which are hereby incorporated by reference in their entirety.

BACKGROUND OF THE INVENTION

1. Field of the Invention

The present invention relates to a housing for shielding and storing a permanent dipole magnet, where the housing includes a mechanism for extending and retracting the magnet from the housing.

2. Description of the Related Art

Strong magnets include electromagnets and permanent magnets. An electromagnet capable of producing a large magnetic field is cumbersome and requires a very large power supply. Permanent magnets exist of relatively compact size that are capable of producing large magnetic fields. However, permanent magnets cannot be turned off and since their polarity is not rapidly switching, they saturate surrounding permeable material and their emitted field is difficult to attenuate. Consequently, permanent magnets are difficult to shield and those that produce large magnetic fields are difficult to handle and store in many settings for which such a magnet might otherwise be useful.

For example, the use of magnetically responsive particles to target drug(s) and/or therapeutic agent(s), device(s) or diagnostic(s) to specific sites through the selective application of a magnetic field, and to achieve prolonged release of high, localized concentrations of drug and/or diagnostic agent by retention of magnetic particles in the region of interest is possible. The externally applied magnetic field produced by a permanent magnet can be used to control the migration and retention of such particles at target sites. However, handling and storage of such a magnet in a clinical setting would be challenging.

SUMMARY

The present invention relates to an apparatus comprising a keeper-shield and a permanent magnet mounted within the keeper-shield. The apparatus renders the magnet easier to store and handle in a variety of settings and for many applications.

In one embodiment, a keeper-shield assembly for housing a magnet comprises a keeper-shield having a central axis and comprising a material substantially permeable to a magnet flux. The keeper-shield assembly further comprises a first cavity in the keeper-shield, the cavity comprising an inner side wall and a base, and the cavity being adapted to accept a core; a core located within the cavity and lining at least part of the inner side wall of the cavity, the core having a second cavity adapted to retractably receive a magnet; a magnet comprising a front and a rear face, the magnet slidably mounted in the second cavity; a lip at an open end of the keeper-shield, the lip extending from an inner side wall of the keeper-shield toward the central axis of the keeper-shield; one or more resilient members configured to contribute a force against the magnet; and a movable actuator extending through the base and configured to contribute a force against the magnet, wherein the movable actuator and the one or more resilient members cooperate to move a portion of the magnet from the retracted position to a position outside of the inner cavity; and wherein the keeper-shield is sufficiently thick so that a magnetic flux density is less than about 100 gauss at a distance of about 2 centimeters from the keeper-shield when the magnet is in a retracted position.

In one embodiment, a keeper-shield assembly comprises a central axis; a plurality of keeper-shields each comprising a material substantially permeable to a magnet flux; a first cavity in each of the keeper-shields, the first cavity in each of the keeper-shields comprising an inner side wall and a base, and the first cavity in each of the keeper-shields being adapted to accept a core that lines part or all of the inner side wall of the first cavity in each of the keeper-shields; each of the cores having a second cavity adapted to accept either a keeper-shield or a magnet; a magnet comprising a front and a rear face, wherein the magnet is slidably mounted in an innermost one of the second cavities; at least one resilient member configured to contribute a force against the rear face of the magnet; and an actuator extending through the base and configured to contribute a force against the rear face of the magnet, wherein a force from the actuator combined with a force from the resilient members moves the magnet from the retracted position to a position wherein a portion of the magnet extends outside of each of the second cavities; and wherein the keeper-shield is sufficiently thick so that a magnetic flux density is less than about 100 gauss at a distance of about 2 centimeters from the keeper-shield assembly when the magnet is in a retracted position.

In one embodiment, a method comprises administering a composition to a patient, the composition comprising magnetic particles; extending a magnet from a keeper-shield to produce a substantially unattenuated magnetic field at a distance of about 2 cm from front face of the keeper-shield; positioning the magnet over a desired location on the patient; and at some time following the administering, retracting the magnet into the keeper-shield to produce at least about 10 fold attenuation of the magnetic field at a distance of about 2 cm from the north pole of the magnet.

In one embodiment, an apparatus comprises means for administering a composition to a patient, the composition comprising magnetic particles; means for extending a magnet from a keeper-shield assembly to produce a substantially unattenuated magnetic field at a distance of about 2 cm from a north pole of the magnet; means for positioning the magnet over a desired location on the patient; and means for retracting the magnet into the keeper-shield to produce at least about 10 fold attenuation of the magnetic field at a distance of about 2 cm from the north pole of the magnet.

The details of the invention are set forth in the accompanying drawings and the description below. Other features, objects and advantages of the invention will be apparent from the description and drawings, and from the claims.

DESCRIPTION OF DRAWINGS

The details of one or more embodiments of the invention are set forth in the accompanying drawings and the description below. Other features, objects, and advantages of the invention will be apparent from the description and drawings, and from the claims.

FIG. 12A is a cross sectional view of a portion of one embodiment of the keeper-shield assembly.

FIG. 12B is a cross sectional view of a portion of another embodiment of the keeper-shield assembly.

FIG. 12C illustrates a cross sectional view of a portion of another embodiment of the keeper-shield assembly 10.

FIG. 12D is a cross sectional view of a portion of yet another embodiment of the keeper-shield assembly, where the magnet is in a retracted position.

FIG. 12E is a cross sectional view of the keeper-shield assembly of FIG. 12D, where the magnet is in an extended position.

FIGS. 16A and 16B illustrate perspective views of another exemplary keeper-shield assembly.

FIG. 18A is an exploded perspective view of an exemplary embodiment of a keeper-shield assembly.

FIG. 18B is a side elevation view of the keeper-shield assembly of FIG. 18A.

FIG. 18C is a rear view of the keeper-shield assembly of FIG. 18A.

FIG. 18D is a cross-sectional view taken across line A—A of FIGS. 18C.

Like reference symbols in the various drawings indicate like elements.

DETAILED DESCRIPTION

According to an embodiment of the invention, a magnet keeper-shield assembly is provided to attenuate the magnetic field of a permanent magnet in areas peripheral to one magnetic pole in an extended, operating position and attenuate the entire magnetic field in a retracted, storage position. The magnet keeper-shield assembly is suited to generate and position a high gradient, non-ionizing magnetic field into deep, targeted tumor sites.

Figure 1:
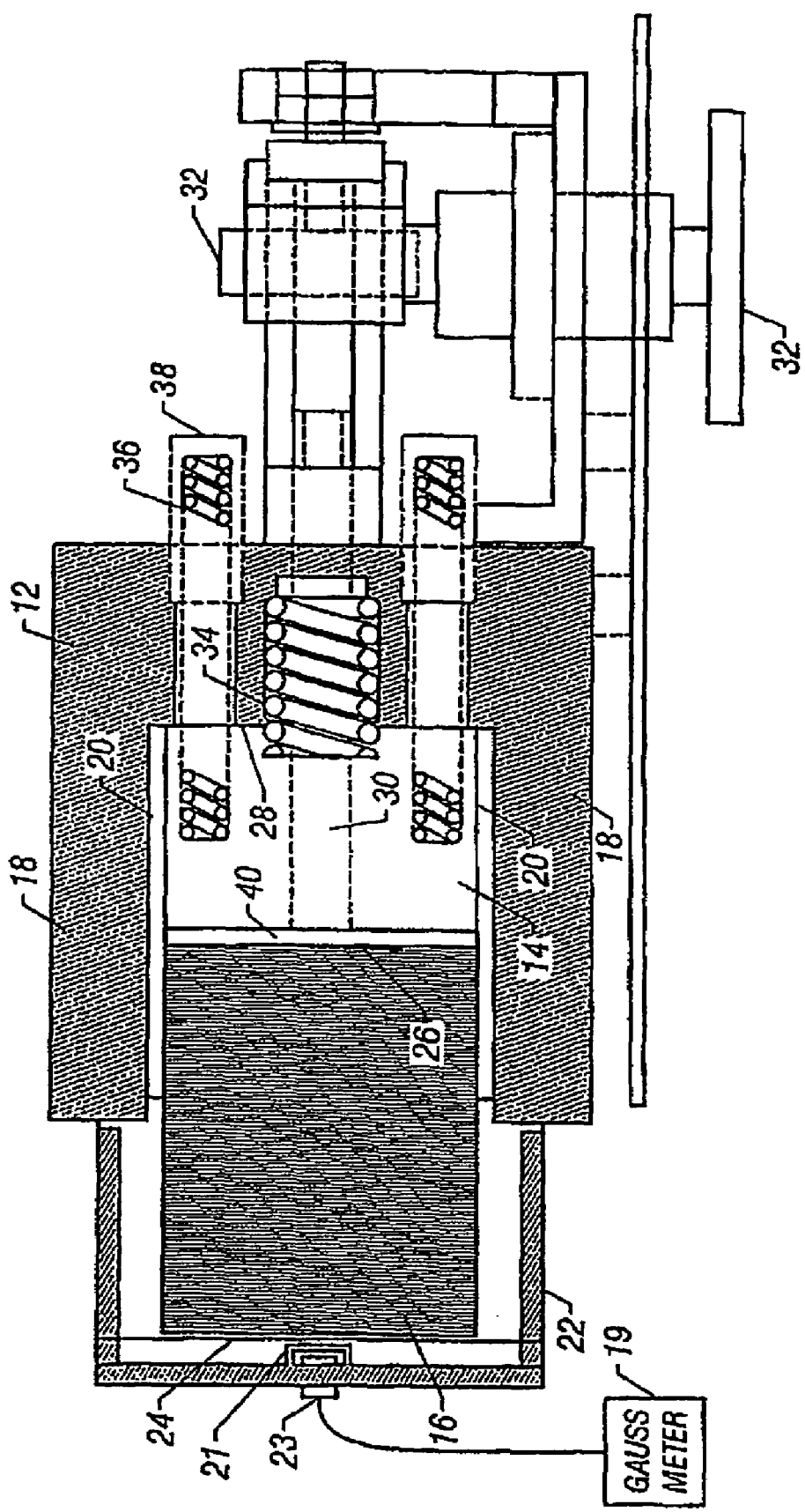
FIG. 1 is a sectional view of a keeper-shield assembly in an extended, operating position according to an embodiment.

FIG. 1 illustrates a magnet keeper-shield assembly 10 according to one embodiment. A keeper-shield 12 approximately 10 cm long is provided with a cylindrical bore 14 dimensioned to accept a cylindrical permanent magnet 16.

The material used in keeper-shield 12 is substantially permeable to magnetic flux. According to the present embodiment, a soft steel, preferably 1010–1018 steel, is used for keeper-shield 12. Other suitable shielding material includes, for example, mumetal (75% Ni—5% Cu—2% Cr—18% Fe) and supermalloy (79% Ni—15% Fe—5% Mo). The keeper-shield material may be laminated. The side wall 18 of keeper-shield 12 has an inner diameter of 5.6 cm and an outer diameter of 8.1 cm. A sleeve 20 of nonmagnetic material is provided along the inner diameter of bore 14 to keep the magnet centered within the bore and prevent surface binding.

A cap 22 may be provided to prevent magnetic objects and debris from magnetically adhering to a north pole 24 of the magnet. Preferably cap 22 is a Delrin cap with an on-axis gaussmeter calibration port 21. The port is a recessed well in the face of the cap positioned over the center axis of north pole 24 of magnet 16. The bottom of the port 21 is 10 cm from the north pole 24, in the retracted position. The port 21 accepts a probe 23, for example a Hall-effect sensor, of a gaussmeter 19 used for measuring the magnetic field at a calibrated distance from the magnet. A magnetic washer 31 can be embedded in the base of the cap to magnetically adhere the cap the keeper-shield 12.

According to an alternate embodiment, cap 22 is constructed from magnetic material and further increases the volume enclosed with-in the 5 gauss line.

Figure 2:
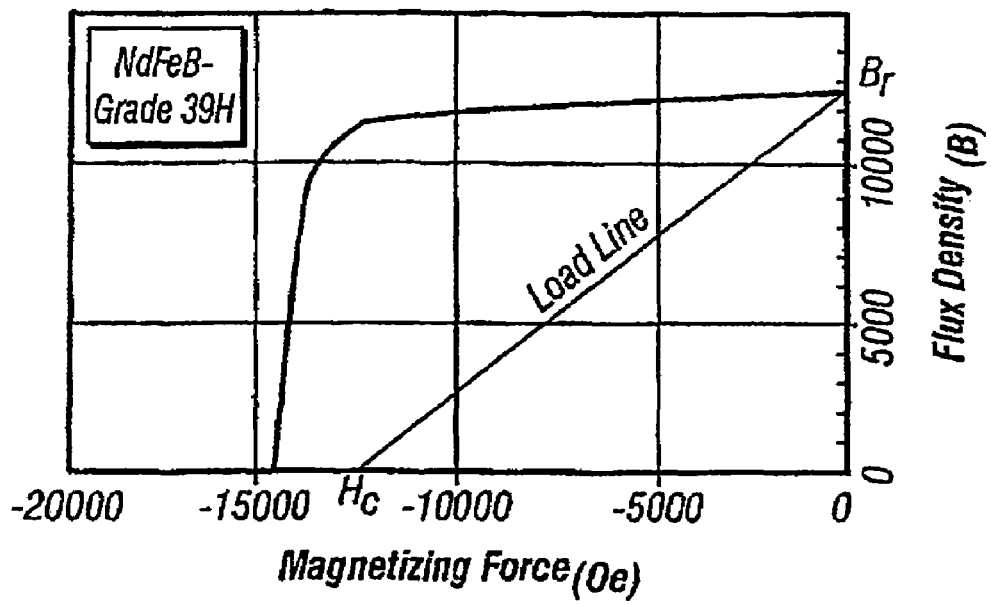
FIG. 2 is a graph showing the de-magnetization curve of the magnet of FIG. 1.

Magnet 16 can be fabricated from any high energy material including Alnico, featuring rare earth (atomic number 21, 39, and 57–71) compositions such as samariam-cobalt and neodymium-iron-boron amongst others, ceramics and ceramic oxides such as amongst others ferrite and garnet compositions and permanent magnet superconductor compositions. According to the present embodiment, the magnet 16 is fabricated from a composition of neodymium-boron-iron ceramic. The magnet is machined to 5.08±0.1 cm dia. by 6.31±0.1 cm length from a powdered metallurgy grade 39H (BHmax at 39 MGOe) (Integrated Magnetics, Culver City, Calif.) composition of Nd2Fe14B that is substantially free of barium and strontium bonding agents. Other grades and compositions of NdFeB are contemplated and appropriate, as well as other magnet dimensions. FIG. 2 illustrates the de-magnetization (B—H) curve for grade 39H neodymium-boron-iron composite. Preferably a sealant is applied to the outer surface of magnet 16 to improve corrosion resistance.

Other compositions of NdFeB, and other rare earth, ceramic, or superconducting magnets may be suitable for magnet 16. For example, stronger magnets may be used to produce a stronger field and increased depth of field at the target site or the same flux at a deeper site. For example, on axis field flux density of magnet 16 (39 MGOe), measured at 10 cm with a Lakeshore (located in Westerville, Ohio), Model 410 gaussmeter, is approximately 112 gauss with a magnetic flux density times magnetic gradient product of approximately 3×10$^3$ gauss 2/cm and the flux density of the magnet 16 is less than approximately 4.5 gauss at 38 cm. The field strength of a magnet of approximately the same dimensions as magnet 16 with a 48 MGOe rating would produce 130 gauss and approximately 4×10$^3$ gauss 2/cm at 10 cm and less than approximately 5 gauss at 38 cm.

Figure 3A:
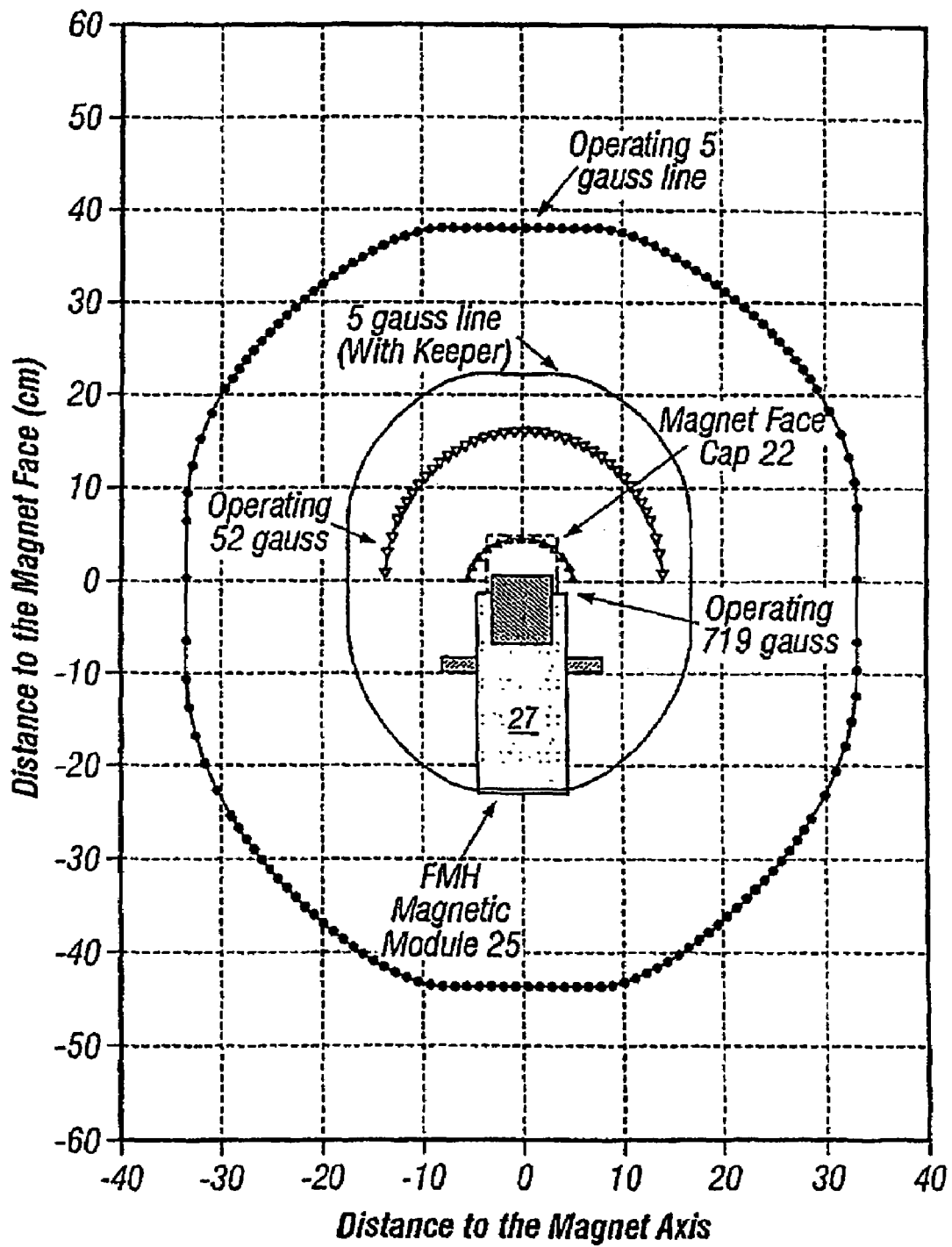
FIGS. 3A and 3B are graphs showing the gradient magnetic field strength of the magnet of FIG. 1.

FIG. 1 illustrates the operating position of the keeper-shield assembly 10 in which magnet 16 extends about 3.5 cm from the front of the keeper-shield 12. FIG. 3A illustrates the magnetic field strength profile around a magnetic module 25 with the magnet 16 in the extended position. The magnetic module 25 includes a dust cover 27 that covers the keeper-shield assembly 10 holding magnet 16. The magnetic field is strongest at front surface 24 and a bottom surface 26, corresponding respectively to the north and south poles of magnet 16.

Front surface 24 may be flat or concave. A concave front face may be provided to focus the magnetic field of the north pole of the magnet. In another embodiment, a convex front face may be provided to broaden the magnetic field of the north pole of the magnet. Additionally, while exemplary embodiments described herein generally refer to the north pole of the magnet 16 extending from the keeper-shield 12, the orientation of the magnet 16 in the keeper-shield assembly 10 may be reversed, thus allowing the south pole of the magnet 16 to extend from the keeper-shield 12. Accordingly, any reference herein to the north pole of the magnet 16 similarly applies to the south pole of the magnet 16 when the orientation of the magnet 16 in the keeper-shield assembly 10 is reversed. Further, the keeper-shield 12 attenuates the magnetic field of the magnet 16 regardless of the orientation of the magnet 16 in the keeper-shield assembly 10. By convention, the north pole is the front surface 24 and the south pole 26 is the bottom surface, it being understood that poles may be interchanged as described above.

Figure 3B:
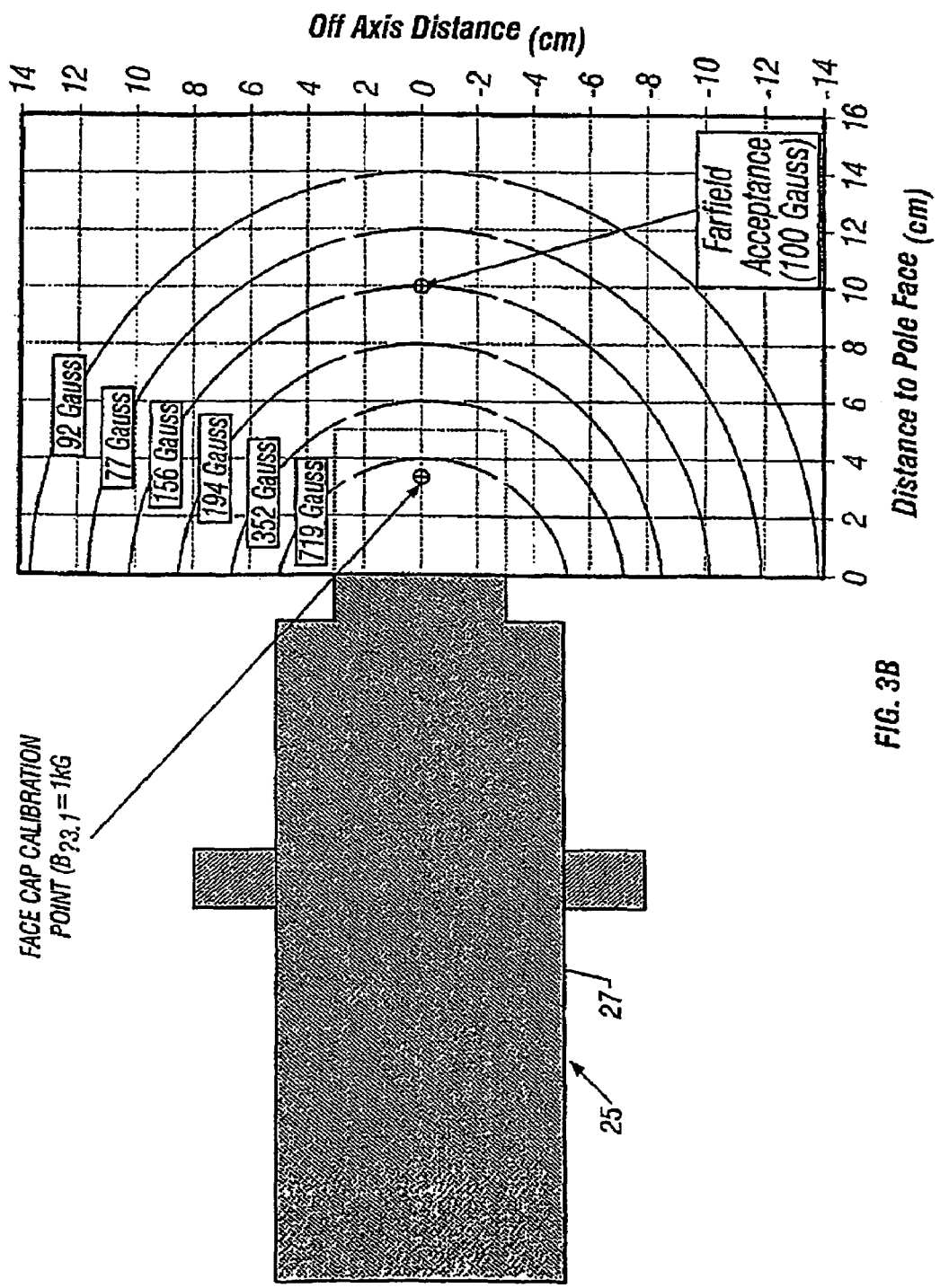

FIG. 3B is a more detailed graph of the magnetic field profile in the operating position. As shown in FIGS. 3A and 3B the magnet produces (on axis) a magnetic flux density of greater than or equal to 50 gauss at 13 cm from the pole face and a magnetic flux density less than or equal to 5 gauss at 38 cm from the pole face 24 in the operating position.

Figure 4:
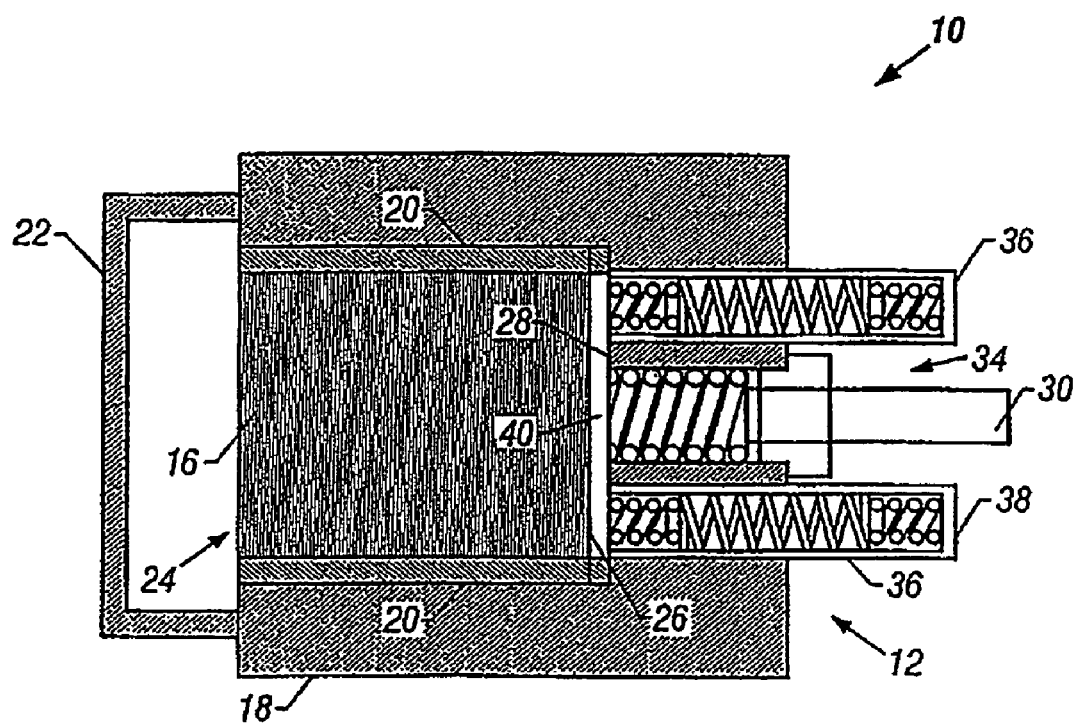
FIG. 4 is a sectional view of the keeper-shield assembly of FIG. 1 in a fully retracted, storage position.

FIG. 4 illustrates the magnet fully retracted in keeper-shield 12 for storage. The magnetically permeable material of the keeper-shield shunts the magnetic field lines, thereby attenuating the magnetic flux around the keeper-shield assembly 10. In the retracted position, the magnet produces 5 gauss at about 22 cm from front face 24. This attenuation of the magnetic flux makes handling and storing the keeper-shield assembly 10 easier, as the attenuation reduces the 5 gauss line to less than 10 cm from the rear of magnetic module 25. Further, the shunting action of the keeper-shield 12 provides long term protection from spurious losses of the field strength. According to the present embodiment, no measurable loss of field strength due to random domain realignment over the life time (at least five years or ten thousand extension/retraction cycles) of the device is expected.

The magnetic field at south pole 26 is comparable to that of north pole 24. The keeper-shield 12 discussed herein provides attenuation of a magnetic field, regardless of the pole orientation of the magnet 16 within the keeper-shield 12. The keeper-shield 12 attenuates the field at the south pole (and/or north pole, depending on magnet orientation and depth of the magnet 16 within the keeper-shield 12), which reduces radiation interference emission and magnetizable object concerns arising from the tendency of magnetic objects to be attracted toward the magnet's poles.

The attractive force between south pole 26 and base 28 of the keeper-shield 12 biases the magnet into the fully retracted position (FIG. 4). An actuator rod 30 is provided through the base 28 to push the magnet 16 out of bore 14. According to the present embodiment, actuator rod 30 is driven by a manually powered screw drive mechanism 32. This mechanism could be motor driven.

Due to the strength of the magnet 16, the attractive force between the south pole 26 and base 28 is very large, and increases approximately proportionally to the inverse of the distance between the south pole 26 and the base 28. The attractive force is greatest in the fully retracted position, at which the attractive force is about 200 pounds.

Figure 5:
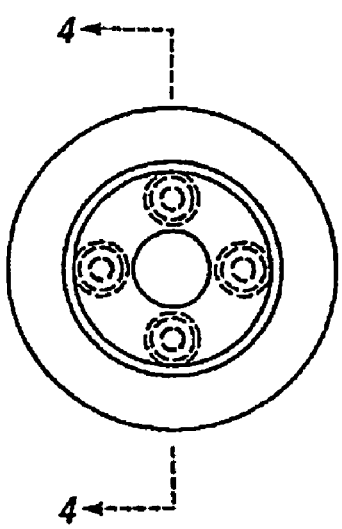
FIG. 5 is a sectional view of the base of the keeper-shield assembly of FIG. 1 showing the position of the springs.

Springs are provided to offset a large portion of this attractive force to ease the action of the actuator rod 30. A relatively strong primary spring 34 is provided in the center of the base around actuator rod 30. Four secondary springs 36 are provided peripherally as shown in FIG. 5, which is a cross-sectional view of the springs 36. Secondary springs are longer than spring 34 and extend through the base 28 into external spring keeper-shield assemblies 38.

A nonmetallic spacer 40 may be provided on south pole 26 to prevent the springs from magnetically adhering to or marrying the south pole 26 of the magnet.

Figure 6:
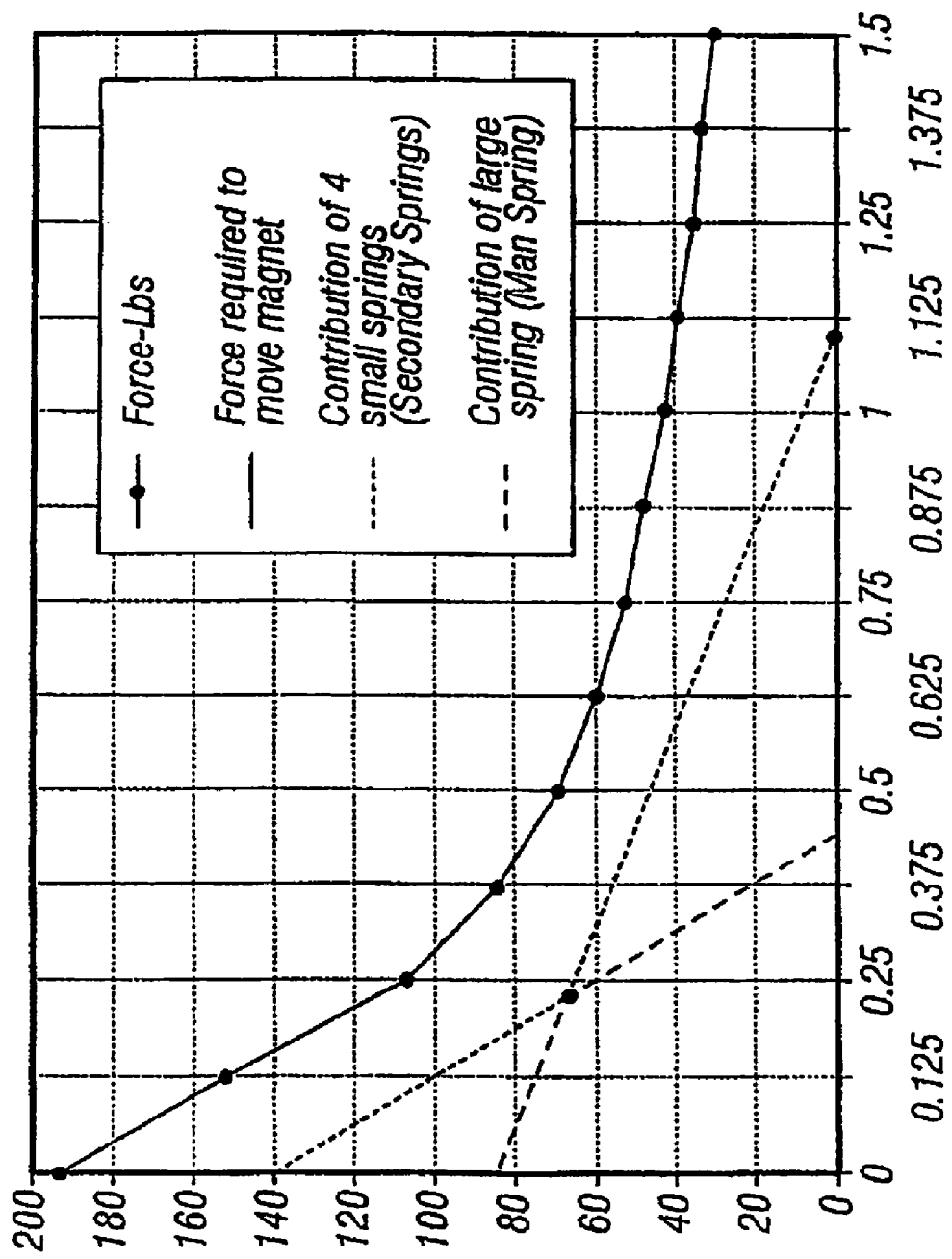
FIG. 6 is a graph showing the force exerted by the springs at different positions of the magnets travel in the keeper-shield assembly of FIG. 1.

The contribution of the springs is cumulative, as shown in FIG. 6. In the fully retracted position, the springs exert a combined force of about 190 pounds on the spacer 40, the primary spring 34 contributing about 95 pounds and secondary springs 36 contributing about 95 pounds. The primary spring 34 contributes the most force up to about 0.25 cm from base 28. After this point the secondary springs 36 contribute the most force. In one embodiment, the user contributes only about 10 lbs of force to initiate movement of the magnet. In other embodiments, the user may contribute up to 40 lbs of force, but preferably is required to contribute less than 20 lbs of force. In order to allow the magnet to be moved with only about 10 lbs of force from the user, springs are selected so that the magnet 16 may be retracted into the keeper-shield assembly 10 (providing attenuation of the magnetic field), but not so far retracted that excessive force is required to extend the magnet 16 from the keeper-shield assembly 10.

The springs only contact the spacer for a portion of the magnet's travel through the bore. Primary spring 34 extends about 0.425 cm into the bore 14 when fully extended, and secondary springs 36 extend about 1.2 cm into the bore 14 when fully extended.

Figure 7:
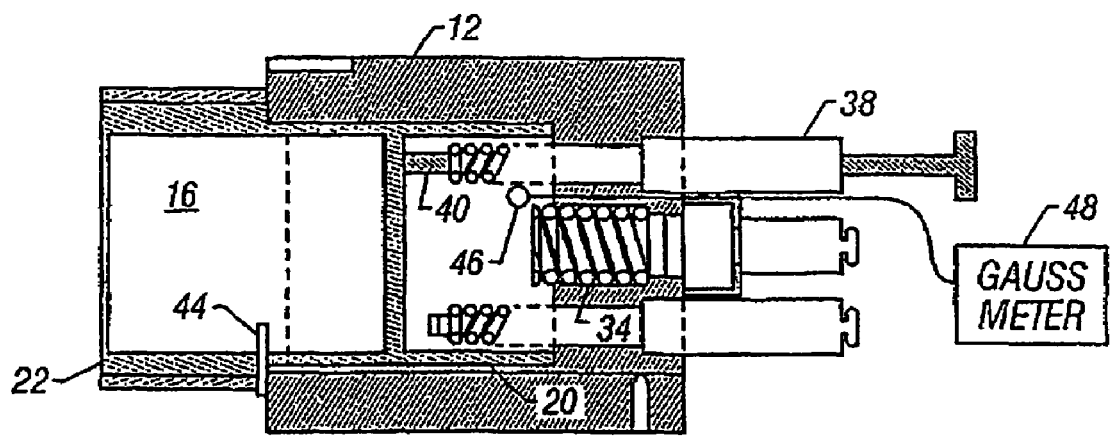
FIG. 7 is a keeper-shield assembly according to another embodiment including a back-up actuator mechanism and magnetic field and magnet position measurement devices.

According to an embodiment shown in FIG. 7, a secondary (back-up) actuator mechanism is provided to extend the magnet in case of failure of the primary actuator mechanism, that is, actuator rod 30 and screw drive mechanism 32. In the event that the primary actuator mechanism fails, a screw that holds a secondary spring in place is removed, and a threaded secondary rod 40 of the same diameter and thread pitch as the removed screw is inserted through the back of keeper-shield 12. Secondary rod 40 is driven by secondary screw drive mechanism to push the magnet 16 out of bore 14.

A sliding position indicator 44 can be attached to the magnet 16 to indicate its position relative to the housing. This allows the user to know the magnet is in the fully extended and fully retracted positions.

A probe 46 for a gaussmeter 48 can be provided at the back of keeper-shield 12. Probe 46 that measures the magnetic field emanated from the south pole face of magnet 16 at that position. As the magnet is extended, the measured field decreases. The measurement is used by a microcontroller 48 to calculate the magnetic field at any distance, for instance 1 cm, from north pole face 24. This allows the user to select a magnetic field strength desired for a particular application continuously over the range of fields emanated between the fully extended and fully retracted magnet positions. In another embodiment, a probe that measures distance or position, such as an ultrasound device is used to measure the distance the magnet has been extended. This distance is then used by a microprocessor to calculate the magnetic field at any distance from the module face.

Figure 8:
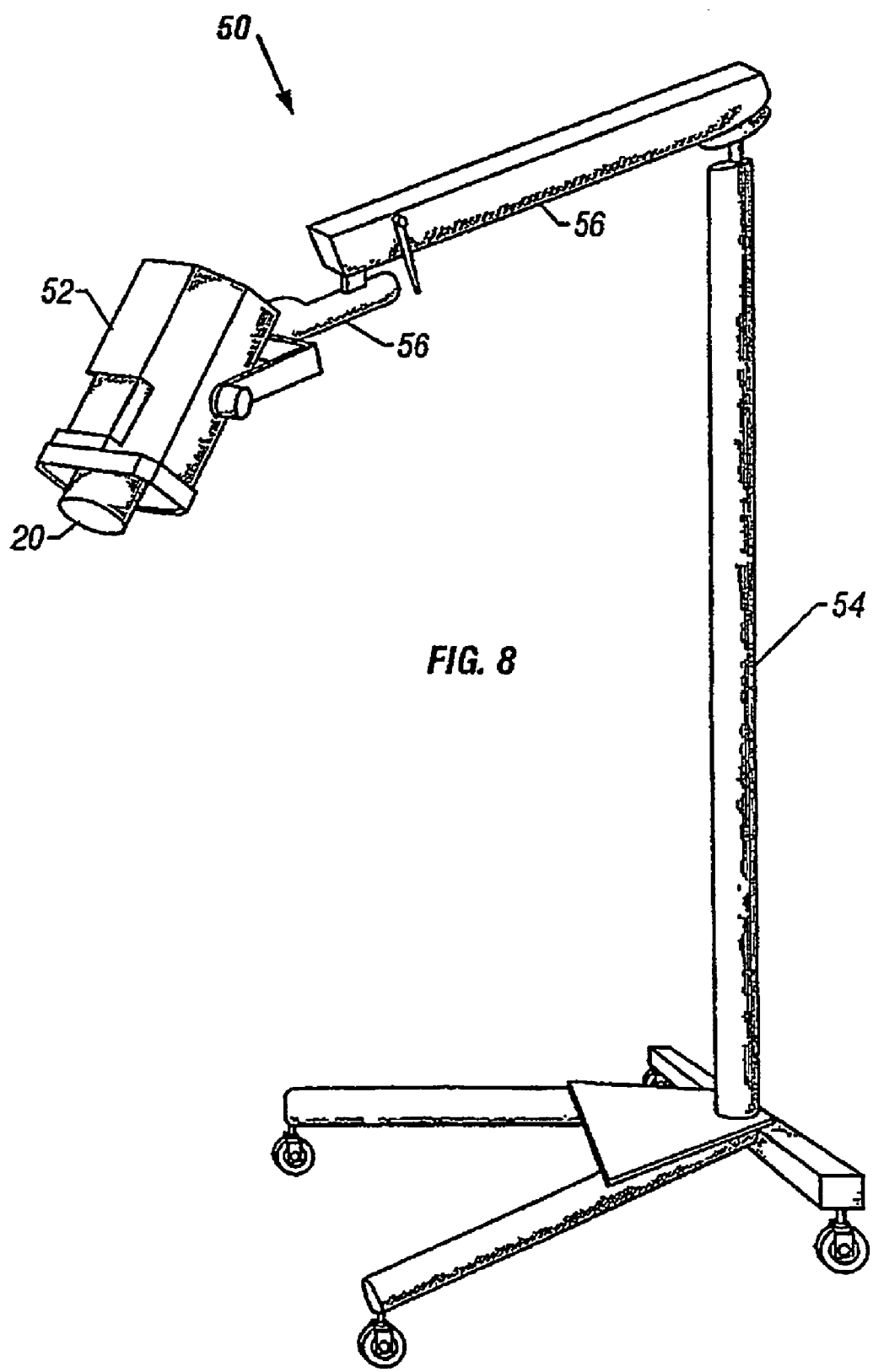
FIG. 8 is a stand according to an embodiment for positioning the keeper-shield assembly.

FIG. 8 illustrates a stand 50 according to an embodiment provided to ease positioning of keeper-shield assembly 10. Keeper-shield assembly 10 is encased in a cover 52 which is attached to a rolling stand 54 by a spring-loaded, counterbalanced articulated arm 56 that can be rotated in three dimensions. The articulated arms 56 and cover 52 may be locked in position to maintain magnet 16 at a desired height and orientation to facilitate precise alignment of the emanated magnetic field onto the targeted site. An articulated magnetic applicator of the type shown in FIG. 8 is supplied by FeRx, Incorporated under the name MagneTarg System™. The MagneTarg System Magnet (MSM) houses and positions the magnetic keeper-shield assembly 10. In another embodiment, the magnet is positioned through an articulating means that is attached to the surgical table or other apparatus for comfortably accommodating a patient. In another embodiment, the magnet is positioned through an articulating means that is attached to the ceiling of the room in which the treatment is to be effected.

Keeper-shield assembly 10 with magnet 16 may be used in conjunction with any magnetic particle for any application. Typically, magnetic particles can be designed to deliver any given drug or diagnostic agent. The use of magnetic particles to deliver antitumor agents may be useful, as described in the following references, each of which is hereby incorporated by reference in their entirety: Pouliquen D, Chouly C., Magnetic microcarriers for medial applications. In: Arshady R. editor. Microspheres microcapsules & liposomes, vol. 2, medical and biotechnology applications, London: Citus Books, 1999. p. 343–82; Widder K J, Senyei A E, Scarpelli D G., Magnetic microspheres: a model system for site specific drug delivery in vivo. Proc Soc Exp Biol Med 1978;58:141–6; Widder K J, Morris R M, Poore G A, Howards D P, Senyei A E., Selective targeting of magnetic albumin microspheres containing low-dose doxorubicin: total remission in Yoshida sarcoma-bearing rats, Eur J Cancer Clin Oncol 1983;19:135–9; Gupta P K, Hung C T. Magnetically controlled targeted microcarrier systems. Magn. Controlled Drug Delivery 1989;44:175–86; Pulfer S K, Gallo J M., Targeting magnetic microspheres to brain tumors, In: Hafeli U, Schütt W, Teller J, Zborowski M, editors. Scientific and clinical applications of magnetic carriers, New York: Plenum Press, 1997, p. 445–55; Lubbe A S, Bergemann C. Selected preclinical and first clinical experiences with magnetically targeted 4'-epidoxorubicin in patients with advanced solid tumors. In: Hafeli U, Schütt W, Teller J, Zborowski M, editors, Scientific and clinical applications of magnetic carriers. New York: Plenum Press, 1997. p. 457–80; Chen H, Langer R S. Magnetically-responsive polymerized liposomes as potential oral delivery vehicles, Pharm Res 1997;14:537–40; and Muller-Schulte D, Fussl F, Lueken H, De Cuyper M. A new AIDS therapy approach using magnetoliposomes, In: Hafeli U, Schütt W, Teller J, Zborowski M, editors, Scientific and clinical applications of magnetic carriers. New York: Plenum Press, 1997, p. 517–26. Further description of ferrocarbon, ferroceramic and magnetopolymer magnetic component particles can be found at Kent et al., U.S. application Ser. No. 10/687,555, filed on Oct. 15, 2003; Rudge et al., U.S. application Ser. No. 09/673,297, filed on Oct. 13, 2000; Tapolsky et al., PCT Application No. PCT/US03/00489, filed on Jan. 7, 2003; and Rudge et al., U.S. Provisional Application No. 60/502,737, filed on Sep. 12, 2003, herein incorporated by reference. The treatment of solid tumors using chemotherapy has been limited by systemic toxicity resulting in sub-optimal dosing, and by multiple other mechanisms (e.g. multiple drug resistance of the tumor cells, tumor architecture limiting access of drug to the tumor cells, volume of distribution for drug) resulting in limited efficacy.

Although the magnet can operate to temperatures up to about 140° C., the preferred operating range of the magnet is from about 10° C. to about 50° C. for such clinical applications.

In order to enhance the effectiveness and diminish systemic toxicities of certain chemotherapeutic agents, investigators have attempted to target administration of these drugs by intra-arterial injection immediately proximal to the tumor. One possible reason why clinically dramatic enhancement of the therapeutic index of an agent like doxorubicin is not observed after administration into a tumor-feeding hepatic arteriole is the lack of retention of the agent at the site. Normal clearance mechanisms lead to rapid elimination of the chemotherapeutic from the region of the tumor and, therefore, only transiently increased levels of the drug are regionally available to exert an antitumor effect. Regional therapy achieved through targeted drug delivery using keeper-shield assembly 10 with magnet 16 could improve efficacy by increasing the drug concentration at the tumor while limiting systemic drug concentrations.

Figure 9:
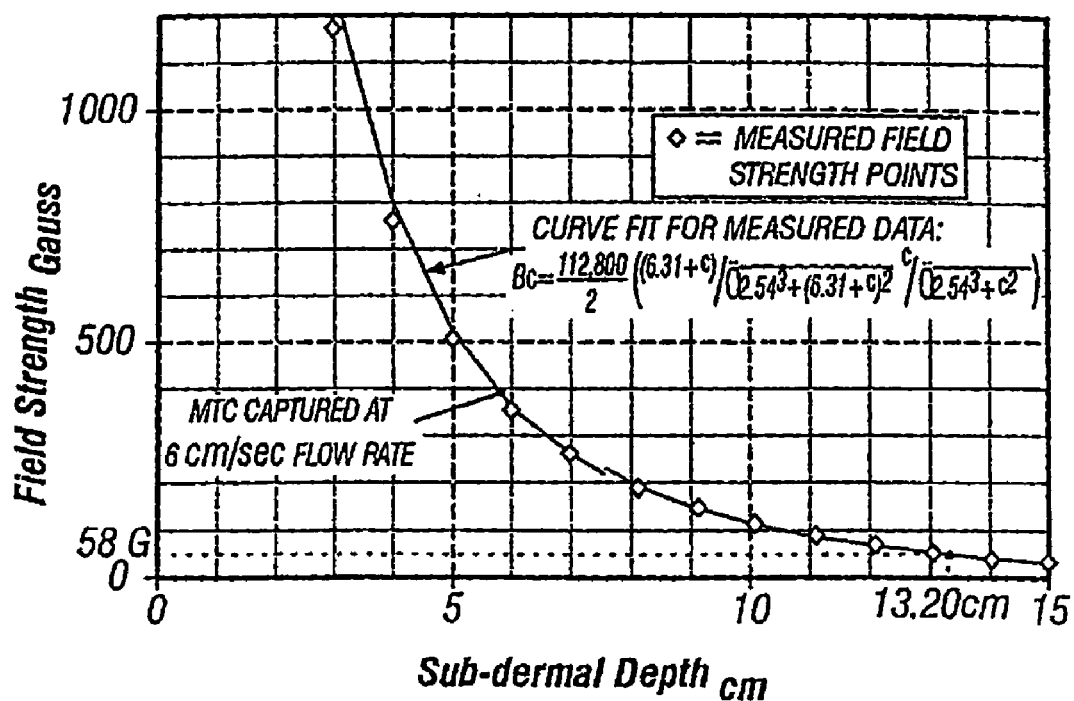
FIG. 9 is a graph showing the field strength as a function of depth in a body.

The keeper-shield assembly 10 is positioned over a target site on the patient. The magnet is extended from the fully retracted position (FIG. 4) to the operating position (FIG. 1) by manipulating screw drive mechanism 32. The keeper-shield assembly 10 and patient are maintained in this position for a prescribed time period that may be from several seconds to many hours. After sufficient exposure, the magnet is retracted to the fully retracted position for storage. FIG. 9 shows the field strength (on axis) of the magnet 16 as a function of on axis distance from the magnet front face.

EXAMPLE 1

Magnetic targeted carriers (MTCs) are a proprietary microsphere composite of elemental iron and activated carbon. See, for example, U.S. Pat. No. 5,549,915 to Volkonsky, issued Aug. 27, 1996; U.S. Pat. No. 5,651,989 to Volkonsky, issued Jul. 29, 1997; U.S. Pat. No. 5,705,195 to Volkonsky, issued Jan. 6, 1998; U.S. Pat. No. 6,200,547 to Volkonsky, issued Mar. 13, 2001; and U.S. Pat. No. 6,482,436 to Volkonsky, issued Nov. 19, 2002. MTCs combine elemental iron and activated carbon in microspheres of 0.5–5 μm. The activated carbon is capable of adsorbing and desorbing a wide variety of drug substances. The elemental iron component of the microspheres allows targeting and local retention after arterial administration, by placement of an external magnet on the body surface. MTC-doxorubicin (MTC-DOX) can thus be administered by selective catheterization of one of the arterioles feeding a tumor. Placement of the external magnet over the region of the tumor allows for efficient targeting of the MTC-DOX. MTC-DOX (doxorubicin) is designed for the magnetically targeted site-specific delivery to a liver tumor in the presence of an externally applied magnetic field.

Eighteen swine were assigned to 6-treatment groups including 3 control groups and 3 doses of the MTC-DOX preparation. Animals were given a single administration of test article and evaluated over 28 days and then sacrificed. There were no adverse effects in the DOX alone group. Biologically significant treatment-related gross and microscopic lesions were limited to the targeted area only of the liver in groups receiving ≧75 mg of MTC, and the "no adverse effect level" NOAEL was determined to be 25 mg MTC/2 mg DOX. Evidence for a possible synergistic effect between MTC and DOX was observed, where parenchyma regenerating from the damage caused by targeted MTCs caused the dividing hepatocytes to be more sensitive to DOX.

Materials

The designation of the test article used was MTC-doxorubicin (MTC-DOX). Doxorubicin-HCl Injection, USP was purchased from Fujisawa USA. The drug carrier was MTC and manufactured by FeRx Incorporated. The MTCs were rendered sterile by gamma irradiation. The vehicle for injection is 10% mannitol and 0.5% carboxymethylcellulose in Water for Injection (WFI). The drug substance (doxorubicin) and vehicle were supplied as sterile solutions, and the drug carrier was supplied as a sterile dry powder. The magnet (1.97 in (w)×2.5 in (1)) housed in the MagneTarg System is a rare-earth NdFeB permanent magnet (39 MGOe).

For administration, a vial containing 100 mg of MTC drug carrier product was incubated at room temperature (18 to 25° C.) with 8 mg (4 mL) of doxorubicin (2 mg/mL) for 30 minutes. The MTC-doxorubicin solution was then diluted with 16 mL of vehicle for injection and sonicated for 30 seconds using a Cole-Palmer Ultrasonic Cleaner using the "Sonic Degas" setting prior to administration. The resulting dose suspension had a concentration of 0.4 mg/ml of doxorubicin and 5.0 mg/ml of MTC drug carrier.

Yorkshire domestic swine used in this study were obtained from S & S Farms (San Diego, Calif.). The animals were laboratory bred and were experimentally naive at the outset of the study. Animals selected for use in this study were as uniform in age and weight as possible. They were generally prepubertal to young adult animals approximately 3 to 4 months of age, and their body weights ranged from 23 to 29 kg. All animals were acclimated to laboratory conditions for a minimum of 7 days prior to study initiation.

Methods

General Description—A total of eighteen animals were randomly assigned to six treatment groups of three animals/group as shown in Table 1 below. Each animal received a single dose of test article by hepatic intra-arterial infusion. The animals were evaluated for changes in clinical signs, body weight, clinical pathology indices, and other parameters as described below. All animals were euthanized on Day 29, except for those animals that required early sacrifice. A full necropsy was conducted on all animals that survived to the end of the study, and a partial necropsy was conducted on those animals that were sacrificed early. A full panel of tissues was collected for histopathological evaluation.

Group Assignments and Dose Levels—Animals were dosed using a fixed concentration of the test article. The low, medium, and high MTC-DOX doses varied as a function of the infusion volume. Table 1 lists the total dose and the mg/kg dose based on the dose calculated from the average pig weight determined for the respective groups.

Catheterization procedure—The animals were fasted overnight (approximately 12–15 hours) prior to surgery. In preparation for the procedure, each animal was weighed and pre-anesthetized with 150 mg ketamine and 150 mg xylazine. The right hind leg of each animal was disinfected with betadine solution and the surgical site was covered with a Steridrape. All study personnel wore surgical gloves, gown or scrubs during the catheterization and administration procedure. Under general anesthesia, a skin incision was made in the right inguinal area and the animals were cannulated via the femoral artery using standard percutaneous techniques. Animals were administered 5000 IU of heparin (Elkins-Sinn) systemically prior to delivery as prophylaxis against catheter induced thrombosis.

Under fluoroscopy, a 5-french angled glide catheter (Cook, Inc., Bloomington, Ind.) and a 0.035 inch angled glidewire (Meditech Inc., Watertown, Mass.) were inserted into the celiac artery. The common or proper hepatic artery was catheterized, and angiography was performed to select a segmental branch of the hepatic artery that provided adequate accessibility to the desired lobe of the liver to which the test article was targeted. The right, middle, or left hepatic artery, or segmental branch thereof, was then catheterized with a Tracker 325 catheter (Target, Inc., Freemont, Calif.) and Taper 22 wire (Target Inc., Freemont, Calif.). Angiography was then performed to verify catheter placement in the desired segmental branch of the hepatic artery feeding the selected lobe of the liver.

Magnet Placement and Depth Measurements—Using angiography, placement of the magnet was determined by placing a 2-inch diameter metal disk on the ventral surface of the pig positioned central to the capillary blush, and approximately 1–2 cm distal to the catheter tip. The disk's position was verified under angiography, and the disk was outlined on the skin surface to guide placement of the magnet. Once the magnet position was determined, a depth from the catheter tip to the center point of the magnet was determined by angiography. For groups 1 and 2, a depth measurement was done by placing a metal ruler on the ventral surface of the skin, distal to the catheter position, and measured by angiography. Following the angiography procedures, the north pole of the 5 kgauss rare-earth magnet housed in the flexible magnet keeper-shield assembly was

TABLE 1

Group assignments and dose levels

| Group No. | Animals/Group | Treatment Group | Dose (mg/kg)[1] Dox | Dose (mg/kg)[1] MTC | Total Dose (mg) Dox | Total Dose (mg) MTC | Dose Volume |
|---|---|---|---|---|---|---|---|
| 1 | 3 | Vehicle Control | 0.00 ± 0.00 | 0.00 ± 0.00 | 0 | 0 | 45 mL |
| 2 | 3 | Dox-High Control | 0.73 ± 0.04 | 0.00 ± 0.00 | 18 | 0 | 45 mL[2] |
| 3 | 3 | MTC-High Control | 0.00 ± 0.00 | 8.85 ± 0.83 | 0 | 225 | 45 mL[3] |
| 4 | 3 | MTC-Dox - Low | 0.08 ± 0.00 | 1.01 ± 0.03 | 2 | 25 | 5 mL[4] |
| 5 | 3 | MTC-Dox - Med | 0.22 ± 0.01 | 2.79 ± 0.16 | 6 | 75 | 15 mL[4] |
| 6 | 3 | MTC-Dox - High | 0.72 ± 0.06 | 8.94 ± 0.71 | 18 | 225 | 45 mL[4] |

[1]The dose in mg/kg was estimated based on the average pig weight for each treatment group.
[2]The dose solution had a concentration of 0.4 mg/ml of doxorubicin.
[3]The dose solution had a concentration of 5.0 mg/ml of MTC drug carrier.
[4]The dose solution had a concentration of 0.4 mg/ml of doxorubicin and 5.0 mg/ml of MTC drug carrier.

centered in the marked position on the surface of the animal. The magnet was kept in position during the entire infusion procedure (groups 3, 4, 5, 6) and for an additional 15 minutes following the completion of the infusion.

Test Material Infusion—The test article dose volume was infused as repeated cycles of 7.5 mL infusions at an infusion rate of 2 mL/min (Group 4 (MTC-DOX low dose group) received a single 5-mL injection), as described in Table 2. The cycles were repeated every 15 minutes until all of the dose volume was administered. Prior to each infusion cycle, the test article suspension was kept uniform by passing the material between two connected syringes 5 times.

common or proper hepatic artery was performed through the 5-french glide catheter to determine the patency of the hepatic arterioles.

Toxicokinetic Analysis—Aliquots of approximately 2.0 mL of whole blood were collected in EDTA-containing tubes from all animals in Groups 2, 4, 5 and 6 on Day 0 prior to dosing, and at 15, 30, 45, 60, 90, 120 and 180 minutes post dose. The samples were mixed immediately by inverting at least six times, and then centrifuged. Analysis of plasma doxorubicin levels were quantitated by HPLC.

TABLE 2

Test material infusion parameters

| Group No. | Treatment Group | Dose Volume | MTC (mg) per Infusion Cycle | Dox (mg) per Infusion Cycle | Volume (mL) per Infusion Cycle | Number of Infusion Cycles |
|---|---|---|---|---|---|---|
| 1 | Vehicle High Control | 45 | 0 | 0 | 7.5 | 6 |
| 2 | Dox-High Control | 45 | 0 | 3 | 7.5 | 6 |
| 3 | MTC-High Control | 45 | 37.5 | 0 | 7.5 | 6 |
| 4 | MTC-DOX - Low | 5 | 25.0 | 2 | 5.0 | 1 |
| 5 | MTC-DOX - Med | 15 | 37.5 | 3 | 7.5 | 2 |
| 6 | MTC-DOX - High | 45 | 37.5 | 3 | 7.5 | 6 |

Post Infusion Angiography—At the end of the infusion, an angiogram was performed to verify the patency of the arteries in the selected lobe of the liver. Angiography was performed through the Tracker 325 catheter. The Tracker 325 was then removed and repeat angiography of the Results Angiography—Table 3 provides information on the location of the target region within the liver, including depth relative to catheter position, and degree of embolization as observed by angiography.

TABLE 3

Post-treatment analysis of embolization

| Group No. | Treatment Group | Animal No. | Liver Segments Targeted | Depth (cm) | | Embolization[2] |
|---|---|---|---|---|---|---|
| 1 | Vehicle Control | 754 | 2, 3, 4 | | 9.5 | – |
| | | 755 | 2, 3, 4 | | 8.6 | – |
| | | 766 | 2, 3, 4, 8 | | 7.1 | NA[3] |
| | | | | Mean | 8.4 | |
| | | | | SD | 0.99 | |
| 2 | Dox Control | 751 | 2, 3, 4, 8 | | 9.1 | + |
| | | 763 | 2, 3, 4 | | 8.4 | – |
| | | 764 | 7, 8 | | 8.3 | – |
| | | | | Mean | 8.6 | |
| | | | | SD | 0.36 | |
| 3 | MTC Control | 750 | 2, 3, 4, 8 | | 9 | + |
| | | 753 | 4, 7, 8 | | 10.8 | ++ |
| | | 761 | 4, 8 | | 10.9 | +++ |
| | | | | Mean | 10.2 | |
| | | | | SD | 0.87 | |
| 4 | MTC-DOX Low | 749 | 2, 3, 4, 8 | | 8.5 | – |
| | | 752 | 2, 3, 4, 8 | | 8.8 | – |
| | | 760 | 2, 3, 4, 8 | | 7.8 | – |
| | | | | Mean | 8.4 | |
| | | | | SD | 0.42 | |
| 5 | MTC-DOX Medium | 723 | 2, 3, 4, 8 | | 9.5 | + |
| | | 756 | 4, 7, 8 | | 11.5 | +/– |
| | | 762 | 2, 3, 4, 7, 8 | | 8 | – |
| | | | | Mean | 9.7 | |
| | | | | SD | 1.43 | |

TABLE 3-continued

Post-treatment analysis of embolization

| Group No. | Treatment Group | Animal No. | Liver Segments Targeted | Depth (cm) | | Embolization[2] |
|---|---|---|---|---|---|---|
| 6 | MTC-DOX High | 748 | 2, 3, 4, 5, 8 | | 8 | +++ |
| | | 757 | 2, 3, 4, 8 | | 11.7 | +++ |
| | | 765 | 4, 7, 8 | | 10 | +++ |
| | | | | Mean | 9.9 | |
| | | | | SD | 1.51 | |

NA = not available
[2]Symbol Definition:
(−) No observed embolization
(+) Minor embolization of selective arterioles
(++) Moderate embolization of selective arterioles
(+++) Significant to complete embolization of selective and main arterioles
[3]End procedure angiography was not done. The animal woke up following the procedure and the catheter had dislodged from the original position.

Figure 11:
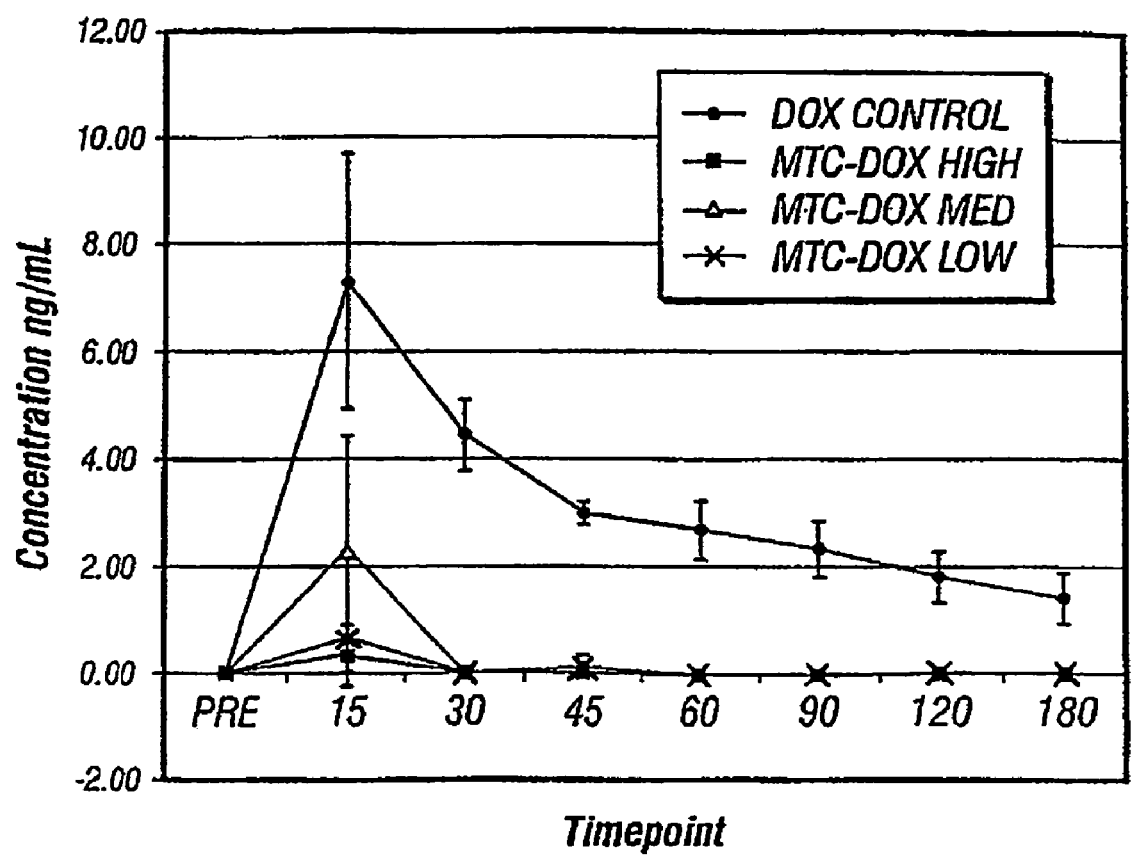
FIG. 11 is toxicokinetic data for patients undergoing injection of magnetic particles having doxorubicin attached thereon and targeted to a desired location in the patient's body through selective application of a magnetic field.

Toxicokinetic Data—Plasma concentrations of doxorubicin were analyzed by HPLC. Samples were taken from Groups 3, 4, 5, and 6 prior to dosing and at 15, 30, 45, 60, 90, 120, and 180 minutes post-dose. Results show that the MTC-DOX groups as compared to the doxorubicin control group have little or no circulating doxorubicin as shown in FIG. 11. These results suggest that the drug remained localized primarily to the targeted site in the MTC-DOX treatment groups.

Microscopic Pathology, Targeted Liver—Direct treatment related microscopic changes were primarily limited to the targeted region of the liver in those groups receiving MTC particles. In general, microscopic changes increased in severity in proportion to the increasing dose of MTC particles, with the most severe liver changes in both groups receiving the high dose of MTC particles (Groups 3 and 6).

As a result of the use of the permanent magnet, extravasation of MTC particles into the portal area tissue (including the walls of the hepatic artery branches) was noted in all animals receiving MTC particles. MTC particles in the Kupffer cells of the hepatic lobule was noted in all groups receiving MTC, although only in one of the three animals (at a minimum severity) in the group receiving the MTC-DOX low dose (group 4). In most animals, multinucleated giant cells were associated with the presence of MTC particles in the portal area tissue.

Several other treatment related changes were present affecting the portal regions of the targeted liver and were present in a dose-related fashion. Portal fibrosis (bridging), a change characterized by bands of fibrous connective tissue connecting adjacent portal areas, was a prominent change except in the MTC-DOX low dose group. Bile duct hyperplasia consistently accompanied the bridging fibrosis.

Bile pigment, peribiliary fibrosis, neutrophilic inflammation of bile ducts and bile duct rupture were variably present in the groups receiving 75 mg of MTC particles or greater (Groups 3, 5, and 6). Chronic/active inflammation was only seen in those animals receiving the high dose of MTC particles (Groups 3 and 6). Of these changes, only mild focal peribiliary fibrosis was present in a single animal receiving the MTC-DOX low dose.

In the targeted liver, severe necrosis of entire hepatic lobules was present in the MTC-DOX high dose group. The MTC control group had moderate necrosis of the targeted region and only one animal in the MTC-DOX Medium dose group had mild necrosis of the hepatic lobules in the targeted liver. Areas of chronic/active inflammation surrounded the areas of necrosis in the MTC-DOX High dose group only. This inflammatory reaction was a response by the body to surround and isolate the zones of necrosis.

Microscopic Pathology, Non-Targeted Liver—In the groups receiving the high dose of MTC particles (Groups 3 and 6), a mild to moderate presence of MTC particles were seen in the hepatic artery, portal areas and hepatic lobules (Kupffer cells) in the non-targeted regions of the liver. The presence of these particles in the non-targeted region of the liver did not appear to cause any associated damage to the liver. Moderate bile-stasis in the non-targeted region of the liver was present in only one animal receiving the MTC-DOX high dose and was considered to be secondary to the severe changes occurring in the targeted region of the liver in that animal. No other groups had particles outside of the targeted region.

Microscopic Pathology, Other Tissues—MTC particles were present within submucosal arteries in the stomach of a single animal in the MTC-DOX High dose group. These particles were associated with a minimal accumulation of multinucleated giant cells but otherwise, there were no related changes in the stomach.

Changes Indirectly Related to Treatment—Microscopic changes indirectly related to treatment were found in the MTC-DOX High dose group only. These changes were present in the lung, heart, and spleen. These changes were inflammatory in nature and likely developed secondary to the clinical deterioration of the animals resulting from the hepatic pathology.

In the lung of two of the three animals from group 6, there was severe lung inflammation with bacteria in the bronchi. These changes were characteristic of a bacterial bronchopneumonia developing either as an acquired infection or via aspiration. In one animal, pleural fibrosis and pleura inflammation was associated with the pneumonia. Neutrophilic inflammation of the pericardium in one of the animals from this group was also most likely due to bacterial infection. Granulomatous inflammation or neutrophilic inflammation in the spleen of 2/3 animals from this group were likely extensions of inflammation in other tissues of the body.

(a) Conclusions

Eighteen female domestic swine were administered a pulsatile administration of one of the following treatments via the hepatic artery: vehicle control (negative control), 18 mg doxorubicin, 225 mg MTC, 25 mg MTC/2 mg doxorubicin, 75 mg MTC/6 mg doxorubicin, or 225 mg MTC/18 mg doxorubicin. Toxicokinetic results indicate that doxorubicin is not freely circulating in any of the MTC-DOX groups, and therefore suggests that the drug has been localized to the targeted site through the use of the externally placed permanent magnet.

EXAMPLE 2

Clinical Engineering at the UCLA Medical Center has evaluated the MagneTarg System lot number D002.

A three-part test was performed to determine its potential effect on the equipment that will be present in angiographic procedure room. The field strength at the face of the MagneTarg System was set at 1,000 gauss.

1. Fluroscopic X-Ray Unit

This test was made to determine the influence of the magnet to the image intensifier at various distances. A line pair resolution phantom was mounted to the center of the image intensifier and successive readings were made. All distance measurements are referenced to the central beam of the image intensifier. For the type of procedure to be performed, an evaluation was made using the 9-inch and 12-inch field modes. In both cases the magnet started to influence the TV image at a 36-inch distance. At 12-inch, the image resolution dropped off completely.

2. Infusion Devices

Various infusion devices were tested within close proximity to the MagneTarg System. The Baxter model 6201, 6301, and PCAII were the only devices affected by the MagneTarg System. When the Magnetic Module was within one inch of these units it caused a "Door Open" alarm, stopping infusion. An example of infusion devices not affected by the MagneTarg System is the Medex 3100 Protege infusion pump.

3. Physiological Monitoring System

The Marquette physiological monitoring system, model Tramscope 12C, was tested within close proximity (up to one inch) to the device without any interference with monitoring performance.

Caution should be used when this device is in close proximity to the above equipment. When the magnet is in the extended position, the Magnetic Module should be at least 36 inches from the X-Ray image intensifier. It should not be used near any implantable devices or respiratory ventilators.

Note that since the maximum field strength of the magnet was measured to be 1,073 gauss, to increase the above mentioned "safe" distances by 10% would be more than sufficient.

It is the UCLA Medical Center Clinical Engineering's recommendation that the MSM is safe to be utilized with human subjects who are not on life support and/or saving devices.

Another aspect of the invention is a method comprising administering a composition including magnetic particles to a patient, extending a magnet from a shielding keeper-shield to produce a substantially unattenuated magnetic field at a distance of about 2 cm from a front face of the keeper-shield, and positioning the magnet over a desired location on the patient. At some time following the administering, the magnet is retracted into the keeper-shield to produce at least about 10 fold attenuation of the magnetic field at a distance of about 2 cm from the front face of the keeper-shield.

In one embodiment, a keeper-shield assembly houses a magnet, the keeper-shield assembly comprising a central axis, a keeper-shield comprising a material substantially permeable to a magnet flux, a first cavity in the keeper-shield, the cavity comprising an inner side wall and a base, and the cavity being adapted to accept a core that lines part or all of the inner side wall of the cavity. The keeper-shield assembly further comprises a core that lines a part or all of the inner side wall and having a second cavity adapted to retractably receive a magnet having a front and a rear face. A magnet comprising a front and a rear face is slidably mounted in the second cavity. The keeper-shield assembly further comprises one or more resilient members configured to contribute a force against the magnet, and a movable actuator extending through the base and configured to contribute a force against the magnet, wherein the movable actuator and the resilient means cooperate to move a portion of the magnet from the retracted position to a position outside of the inner cavity when the actuator is moved, and wherein the keeper-shield is sufficiently thick so that a magnetic flux density is less than about 100 gauss at a distance of about 2 centimeters from the keeper-shield when the magnet is in a retracted position. The actuator may comprise one of many devices capable of applying a force to the magnet so that the magnet is moved relative to the keeper-shield. FIGS. 15–17 illustrate exemplary keeper-shield assemblies having actuators that may advantageously be operated manually in order to move the magnet relative to the keeper-shield. FIG. 12A illustrates a side cross sectional view of a portion of one embodiment of a keeper-shield assembly 10A. The keeper-shield assembly 10A, as shown in FIG. 12A, illustrates the arrangement of the non-magnetic sleeve 20 and the keeper-shield 12. As discussed above, the non-magnetic sleeve 20 extends about the outer circumference of the magnet 16 and is configured to maintain the position of the magnet 16 in the center of the keeper-shield 12 and prevent the magnet 16 from binding with the keeper-shield 12. The non-magnetic sleeve 20 may comprise, for example, plastic, including polyethylene, polyurethane, or nylon; aluminum; or teflon.

Table 4, below, shows the magnetic flux density measured at various distances from keeper-shield assembly 10A. The first column in Table 4 provides flux density (in gauss) measurements of a bare magnet at distances of 2 to 34 cm from the bare magnet. The remaining columns provide magnetic flux density (in gauss) measurements at distances from 2 to 34 cm from the keeper-shield assembly 10A with the magnet in the extended and retracted positions. As shown in Table 4, when the magnet 16 is in the extended position, such as in FIG. 1, the magnetic flux density is about 2010 gauss at 2 cm, 35.2 gauss at 16 cm, and 4.57 gauss at 34 cm from the magnet 16 or nearly identical to a bare magnet. When the magnet is in the retracted position, such as in FIGS. 4 and 12A, the magnetic flux density is about 201 gauss at 2 cm and 5.37 gauss at 16 cm from the magnet 16.

TABLE 4

Magnetic Flux Density of Keeper-Shield Assembly 10A

| Distance from keeper-shield assembly (cm) | Bare Magnet (reference) Magnetic Flux (G) | Extended Magnetic Flux (G) | Retracted Magnetic Flux (G) |
| --- | --- | --- | --- |
| 2 | 2048.6 | 2010.00 | 201.00 |
| 4 | 754.7 | 757.67 | 88.73 |
| 6 | 341.8 | 348.33 | 45.90 |
| 8 | 181.3 | 187.00 | 26.47 |

TABLE 4-continued

Magnetic Flux Density of Keeper-Shield Assembly 10A

| Distance from keeper-shield assembly (cm) | Bare Magnet (reference) Magnetic Flux (G) | Extended Magnetic Flux (G) | Retracted Magnetic Flux (G) |
|---|---|---|---|
| 10 | 107.2 | 112.33 | 16.50 |
| 12 | 68.6 | 72.43 | 10.93 |
| 14 | 46.5 | 49.40 | 7.57 |
| 16 | 32.9 | 35.20 | 5.37 |
| 18 | 24.2 | 26.00 | |
| 20 | 18.3 | 19.77 | |
| 22 | 14.2 | 15.27 | |
| 24 | 11.2 | 12.10 | |
| 26 | 9.0 | 9.77 | |
| 28 | 7.3 | 7.93 | |
| 30 | 6.1 | 6.57 | |
| 32 | 5.1 | 5.40 | |
| 34 | 4.3 | 4.57 | |

FIG. 12B illustrates a side cross sectional view of a portion of another embodiment of a keeper-shield assembly 10B. The keeper-shield assembly 10B, illustrated in FIG. 12B, comprises a non-magnetic core 60 that has a thickness greater than the sleeve 20 in FIG. 12A. In one embodiment, the non-magnetic core 60 comprises one or more non-magnetic materials, similar to the sleeve 20. However, because of the thickness of the non-magnetic core 60, the core 60 advantageously increases the distance between the keeper-shield 12 and the magnet 16 so that, when the magnet is in the fully retracted (as shown in FIG. 12B) or partially retracted position, the magnetic field that emanates from the keeper-shield assembly 10B is reduced. In one embodiment the core 60 is secured in the keeper-shield assembly so that as the magnet moves between the extended and retracted positions, the core 60 remains stationary. In one embodiment, a lip 62 (described further below) is positioned to hold the core 60 in place. In contrast, in one embodiment, the sleeve 20 of FIG. 12A may move relative to the keeper-shield 12 as the magnet 16 is moved between the extended and retracted positions.

In another embodiment, the thickness of the core may be chosen so as to attenuate the magnetic field of any magnet when that magnet is withdrawn into the bore of the keeper. In one embodiment, the dimensions of the sleeve and core are selected to provide attenuation of the magnet contained therein. For example, in one embodiment, the attenuation of the magnetic field when the magnet is in the retracted position is greater than about 10 fold when measured at short distance, for instance 2 cm, from the north pole of the magnet. In embodiments in which the dimensions of the sleeve and core are selected with a different magnet in mind, the set of springs selected to help extend the magnet are changed to allow for 10 lbs residual extension force required from the user.

Table 5, below, shows the magnetic flux density measured at various distances from keeper-shield assembly 10B. A first column in Table 5 provides flux density (in gauss) measurements of a bare magnet at distances of 2 to 34 cm from the bare magnet. The remaining columns provide magnetic flux density (in gauss) measurements at distances from 2 to 34 cm from the keeper-shield assembly 10B with the magnet in the extended and retracted positions.

The magnets 16 used in the measurements listed in Tables 4 and 5 have substantially identical magnetic properties. Thus, any differences in magnetic flux densities in the two tables is primarily due to the configuration and relative arrangement of the magnet 16, non-magnetic sleeve 20 (FIG. 12A; Table 4), non-magnetic core 60 (FIG. 12B; Table 5), and the keeper-shield 12 as illustrated in FIGS. 12A and 12B.

As illustrated in Table 5, when the magnet 16 is in the extended position, such as in FIG. 1, the magnetic flux density is about 2020 gauss at 2 cm, 35.17 gauss at 16 cm, and 4.8 gauss at 34 cm from the magnet 16. Thus, as indicated by the figures listed in Tables 4 and 5, when the magnet 16 is in the extended position a substantially identical magnetic field is produced within each keeper-shield assembly configuration. The magnetic field is also substantially equivalent to that measured on the same magnet held without a keeper/shield (compare the Bare Magnet and Extended measurements in Tables 4 and 5). However, when the magnet is retracted in the keeper-shield assembly 10B the magnetic field is substantially less than when the magnet is retracted in the keeper-shield assembly 10A (comparing the magnetic field measured at the same distances from each of the keeper-shield assemblies 10A and 10B).

As illustrated below in Table 5, using the keeper-shield assembly 10B, when the magnet 20 is in the retracted position, the magnetic flux density is about 97.4 gauss at 2 cm and 3.2 gauss at 16 cm from the magnet 16. Thus, the magnetic flux density surrounding the keeper-shield assembly 10B (including the non-magnetic core 60) is about half that of the keeper-shield assembly 10A. More particularly, the non-magnetic core 60 advantageously increases the distance between the keeper-shield 12 and the magnet 16 so that, when the magnet is in the fully retracted or partially retracted position, the magnetic field that emanates from the keeper-shield assembly 10B is reduced. As such, the embodiment in FIG. 12B advantageously reduces magnetic interactions with magnetically susceptible objects when the magnet is in the retracted position. This may be advantageous because many high value items that may be used in proximity to the magnet 16 are magnetically susceptible and unfavorably influenced by strong magnetic fields. For example, liquid crystals, cathode ray tubes, electromotive devices such as motors, pumps and solenoids, and implanted medical devices, such as pacemakers and ventricular-peritoneal shunts, may be affected by magnetic fields. The attenuation of the magnetic field may also advantageously reduce the capacity of the keeper-shield assembly 10 to attract sharp or heavy metal (magnetic) objects, particularly those that might be found in a patient, for instance metal filings that are sometimes found around the optic nerves of metal tool workers.

TABLE 5

Magnetic Flux Density of Keeper-Shield Assembly 10B (including non-magnetic core 60)

| Distance from keeper-shield assembly (cm) | Bare Magnet (reference) Magnetic Flux (G) | Extended Magnetic Flux (G) | Retracted Magnetic Flux (G) |
|---|---|---|---|
| 2 | 2048.6 | 2020.00 | 97.47 |
| 4 | 754.7 | 760.33 | 43.47 |
| 6 | 341.8 | 349.00 | 22.97 |
| 8 | 181.3 | 187.00 | 13.67 |
| 10 | 107.2 | 112.20 | 8.73 |
| 12 | 68.6 | 72.33 | 5.97 |
| 14 | 46.5 | 49.33 | 4.30 |

TABLE 5-continued

Magnetic Flux Density of Keeper-Shield Assembly 10B
(including non-magnetic core 60)

| Distance from keeper-shield assembly (cm) | Bare Magnet (reference) Magnetic Flux (G) | Extended Magnetic Flux (G) | Retracted Magnetic Flux (G) |
| --- | --- | --- | --- |
| 16 | 32.9 | 35.17 | 3.20 |
| 18 | 24.2 | 26.00 | |
| 20 | 18.3 | 19.77 | |
| 22 | 14.2 | 15.43 | |
| 24 | 11.2 | 12.27 | |
| 26 | 9.0 | 9.83 | |
| 28 | 7.3 | 8.13 | |
| 30 | 6.1 | 6.73 | |
| 32 | 5.1 | 5.67 | |
| 34 | 4.3 | 4.80 | |

The embodiment illustrated in FIG. 12B additionally includes a lip 62 that is located at the open end of the keeper-shield assembly 10 and extends from the keeper-shield 12 inward toward the magnet 16. In one embodiment, the lip 62 is positioned to hold the core 60 in place and also configured to further attenuate the magnetic field when the magnet 16 is in the retracted position. As described above, keeper-shield 12 comprises a material that is substantially permeable to magnetic flux. Thus, the lip 62, which also comprises material that is substantially permeable to magnetic flux, further attenuates the magnetic field produced by the magnet 16. Accordingly, when the magnet 16 is in the retracted position (FIG. 12B) the magnetic field surrounding the keeper-shield assembly 10B is attenuated by the lip 62. Additionally, a material that is substantially permeable to magnetic flux may be placed over the bore aperture of any of the keeper-shield assemblies 10A–F when the magnet is retracted to further attenuate the magnetic field. For example, a disk fitted over the bore aperture may provide a substantially complete shield around the magnet, such that the magnetic flux around the keeper-assembly 10B is further reduced. Such a cover may be implemented in any way known in the art, such as, for example, a spring loaded cover that automatically closes when the magnet 10B is place in the retracted position.

Figure 10:
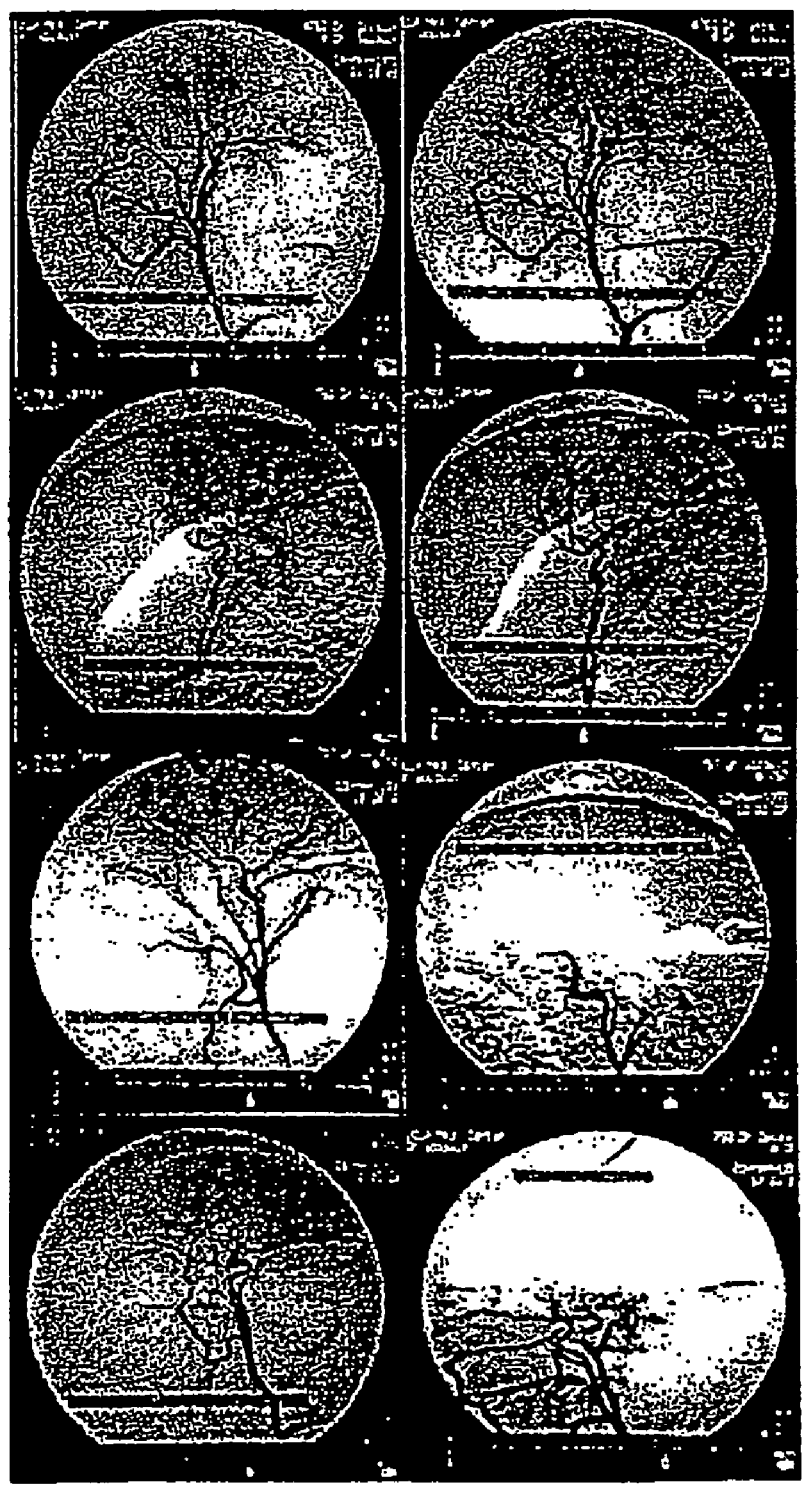
FIG. 10 is pre-(left panels) and post-(right panels) dose angiographies of hepatic arteries for magnetic targeted carriers having various concentrations of doxorubicin adsorbed thereon (MTC-DOX).

FIG. 12C illustrates a side cross sectional view of a portion of another embodiment of a keeper-shield assembly 10C. The keeper-shield assembly 10C, illustrated in FIG. 12C, comprises a non-magnetic core 60, a keeper-shield 12, and a magnet 16. The magnet 16 of FIG. 12C is shown in a retracted position within the keeper-shield assembly 10C. FIG. 12C additionally includes broken lines 17 indicating another position of the magnet 16 within the keeper-shield assembly 10C. As shown in the exemplary embodiment of FIG. 12C, there are various stages of retraction of the magnet 16 into the keeper-shield 12. For example, in one embodiment, the magnet 16 may be retracted in the keeper-shield 12 to an equilibrium position, such as the position of the magnet 16 in FIG. 10C. In another embodiment, the magnet 16 may be retracted (or allowed to retract) only to the position indicated by broken lines 17, which may not be the equilibrium position of the magnet, in order to allow the magnet to be extended using less force than is required to move the magnet from its equilibrium position. Thus, there is typically a compromise between the shielding provided by the keeper-shield 12 and the force required to extend the magnet from the keeper-shield 12. More particularly, as the magnet is allowed to retract deeper into the keeper-shield 12, the shielding provided by the keeper-shield 12 is increased. However, as the magnet is allowed to retract deeper into the keeper-shield 12, the force required to move the magnet from a position that is closer to the equilibrium position within the keeper-shield 12 to the extended position is increased. Thus, the retracted position of the magnet 16 within the keeper-shield 12 may vary in different embodiments and when used in various applications.

While the advantages of having a core 60 and lip 62 have been discussed together above (FIGS. 12B and 12C), one of skill in the art will recognize that either structural feature will provide similar results, while the combination of the two features provides additionally advantageous results. Thus, an embodiment of the keeper-shield assembly comprising a core 60, but no lip 62, attenuates the magnetic field to a greater extent than in an embodiment not having the core 60. Likewise, an embodiment of the keeper-shield assembly comprising a lip 62, but no core 60, attenuates the magnetic field to a greater extent than in an embodiment not having the lip 62. Also, the addition of a magnetically permeable cover across the bore aperture may alone, or in combination with a core 60 and/or lip 62, further attenuate the magnetic field emanated from the magnet 16 retracted in the keeper-shield assembly.

Another aspect of the invention is a keeper-shield assembly comprising a central axis, more than one keeper-shield comprising a material substantially permeable to a magnet flux, a first cavity in each of the keeper-shields, the cavity comprising an inner side wall and a base, and the cavity being adapted to accept a core that lines part or all of the inner side wall of the cavity, said core having a second cavity adapted to accept a magnet having a front and a rear face, a magnet comprising a front and a rear face slidably mounted in the innermost of the second cavities, and one or more resilient members configured to contribute a force against the rear face of the magnet. In one embodiment, the one or more resilient members comprises one or more springs, hydraulics, pneumatics, or motors, for example. The keeper-shield assembly further comprises an actuator extending through the base and configured to contribute a force against the rear face of the magnet, wherein a force from the actuator combined with a force from the resilient members moves a portion of the magnet from the retracted position to a position outside of the inner cavity, and wherein the keeper-shield is sufficiently thick so that a magnetic flux density is less than about 100 gauss at a distance of about 2 centimeters from the keeper-shield when the magnet is in a retracted position, further wherein there are more than one pair of keeper-shields and cores nested within each other around the central axis, the innermost of which has a second cavity that contains the magnet. This embodiment is described in further detail below with respect to FIGS. 12D and 12E.

FIGS. 12D and 12E are side cross sectional views of a portion of another embodiment of a keeper-shield assembly. In FIG. 12D the magnet 16 is in a retracted position and in FIG. 12E the magnet 16 is in an extended position. In the embodiment of FIGS. 12D and 12E, the keeper-shield assembly 10 (10D and 10E) comprises multiple cores 104 (including cores 104A, 104B, and 104C) and multiple shields 102 (including shields 102A, 102B, and 102C). In one embodiment, the cores 104 and shields 102 are made alternatively of non-magnetic and highly magnetic permeable materials in order to further attenuate the magnetic field of the magnet 16. In an exemplary embodiment, the cores 104 comprise non-magnetic material, such as plastic, including polyethylene, polyurethane, or nylon; aluminum; or teflon, and the shields 102 comprise a metal, such as iron or an alloy, such as a Mu metal or supermalloy which allows magnetic lines of force to concentrate within it, thus freeing the space outside the alloy of high permeability of those force lines which would otherwise constitute a magnetic field. Thus, in one embodiment, the shields 102 shield the magnetic field of the magnet 16 while the cores 104 provide spacing between the multiple shields 102. It is contemplated that any number of layers of cores 104 and shields 102 may be used to provide a shielding effect. For example, one embodiment comprises one core 104 surrounded by shields 102 on either side. Additionally, the thickness of the cores 104 and shields 102 need not be the same.

Figure 12F:
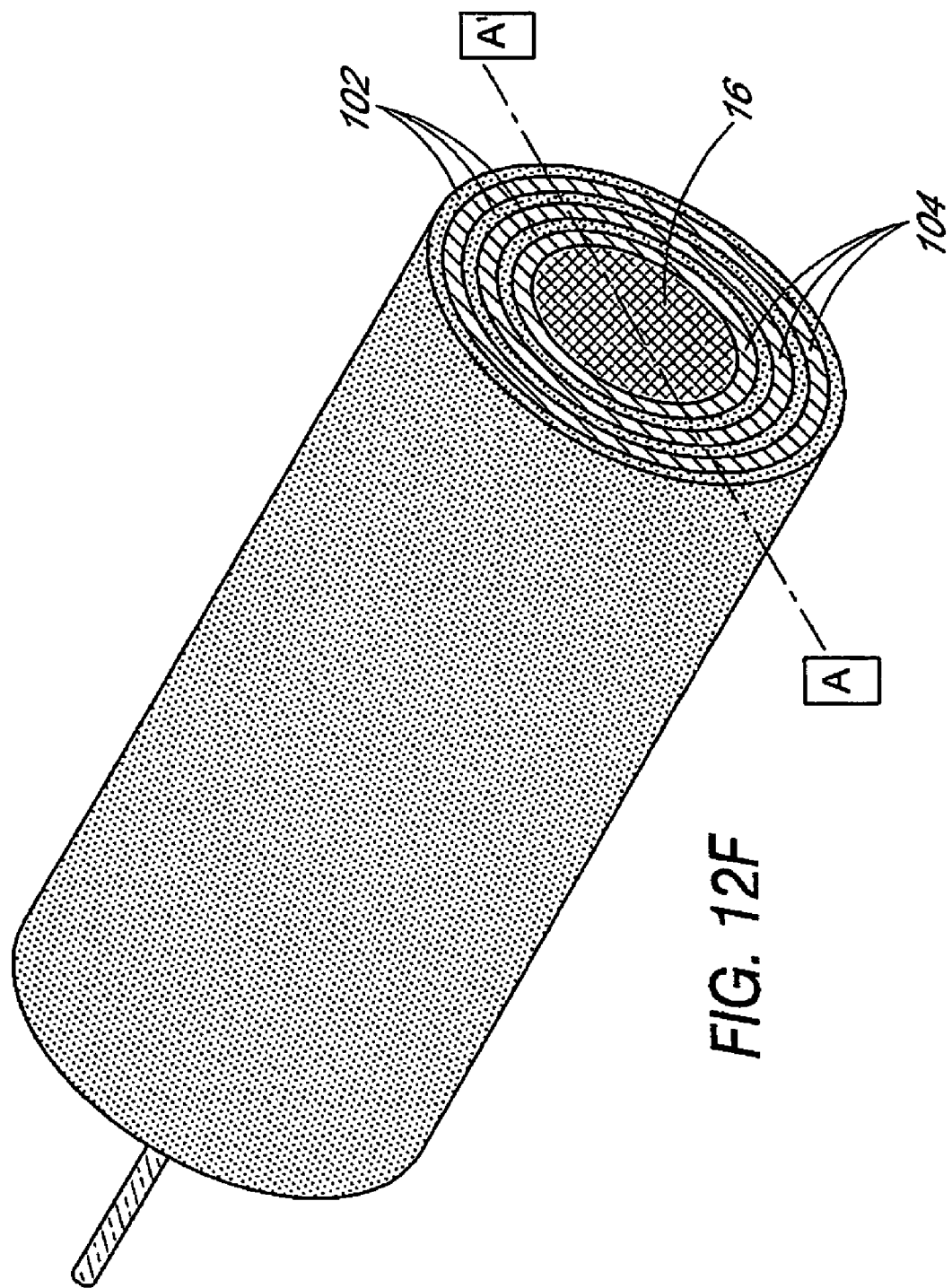
FIG. 12F is a cross section along the line A–A' of FIG. 12D.

FIG. 12F is a perspective view illustrating a cross section taken along the line A–A' of FIG. 12D. As illustrated in FIG. 12F, the magnet 16 is surrounded on all sides by multiple layers of cores 104 and shields 102. As discussed above, the cores 104 and shields 102 may have different thicknesses and any number of cores 104 and shields 102 may provide attenuation of a magnetic field emanated from the magnet 16.

Figure 13:
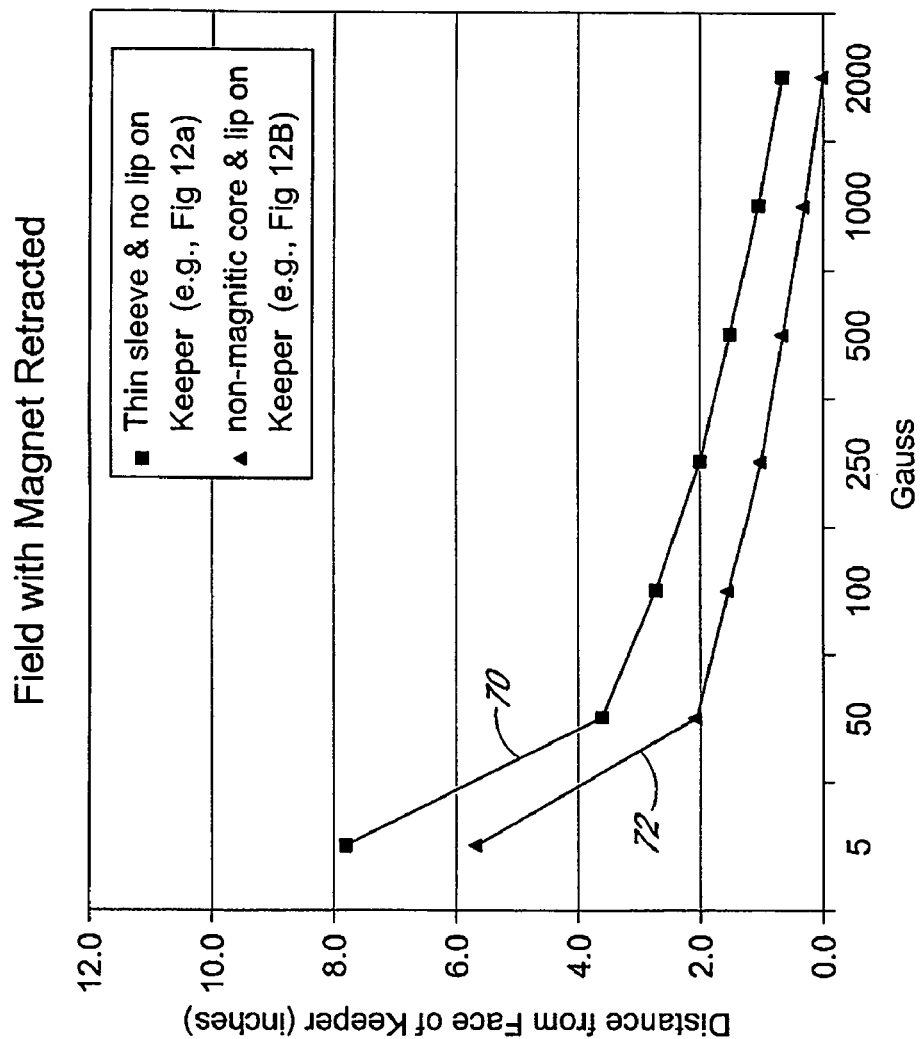
FIG. 13 is a graph illustrating the magnetic flux density surrounding two embodiments of keeper-shield assemblies with the magnets in the retracted position.

FIG. 13 is a graph illustrating the magnetic flux density surrounding two embodiments of keeper-shield assemblies, with the magnet 16 in the retracted position. Specifically, the vertical axis of the graph defines the distance from the face of the keeper-shield assembly 10 (in inches) and the horizontal axis defines the magnetic flux density (in gauss). The connecting line 70 connects data points obtained by measuring the magnetic flux density of a keeper-shield assembly having a thin sleeve 20, such as in FIGS. 1, 4, and 12A, for example. The connecting line 72 connects data points obtained by measuring the magnetic flux density of a keeper-shield assembly having a core 60 and a lip 62, such as in FIG. 12B, for example. As shown in FIG. 13, the magnetic flux density at any particular distance from the keeper-shield assembly with the core 60 and the lip 62 (connecting line 72) is less than the magnetic flux density measured at the same distance from the keeper-shield assembly without the core 60 and without the lip 62.

Figure 14:
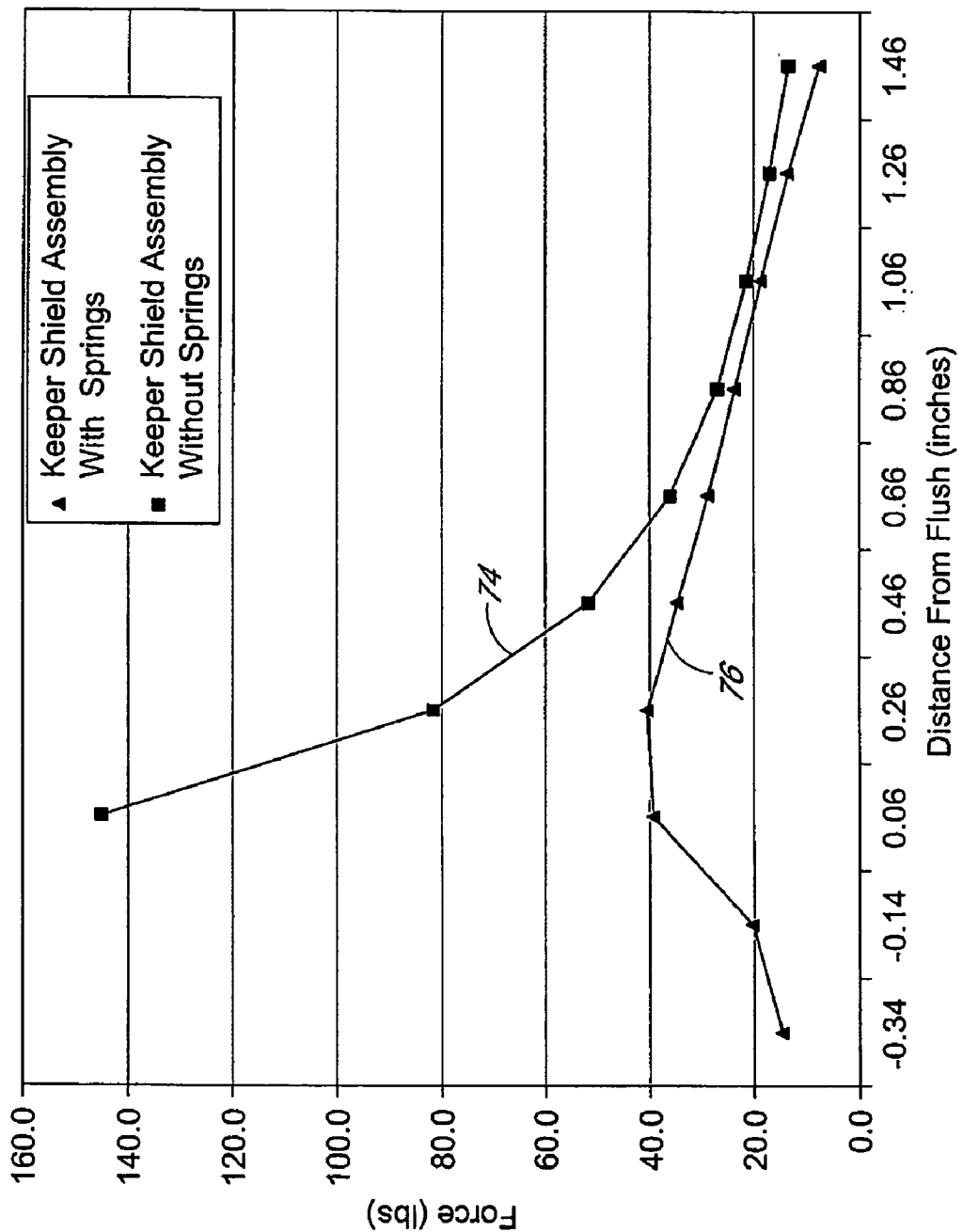
FIG. 14 is a graph illustrating the attractive force (in pounds) of the magnet towards the keeper-shield assembly.

FIG. 14 is a graph illustrating the attractive force (in pounds) of the magnet 16 toward embodiments of the keeper-shield assembly, including the base 28 (FIG. 1). The connecting lines 74 and 76 each connect data points obtained by measuring the force exerted by the magnet 16 toward embodiments of keeper-shield assemblies having a core 60 and a lip 62, such as in FIG. 12B, for example. More particularly, the connecting line 76 connects data points obtained by measuring the force exerted by a magnet 16 toward a keeper-shield assembly including springs configured to contribute a force in a direction opposite to the retractive force of the magnet 16 toward the keeper-shield 12. The connecting line 74 connects data points obtained by measuring the force exerted by the magnet 16 toward a keeper-shield assembly where no springs are used to contribute a force against the magnet. As indicated in the graph of FIG. 14, the force exerted by the magnet 16 toward the keeper-shield 12 including springs is much less than the force exerted by the magnet 16 toward a keeper-shield assembly without springs. Accordingly, the magnet 16 may be more easily moved in and out of the keeper-shield assembly in an embodiment including springs configured to contribute a force against the magnet 16.

Figure 15A:
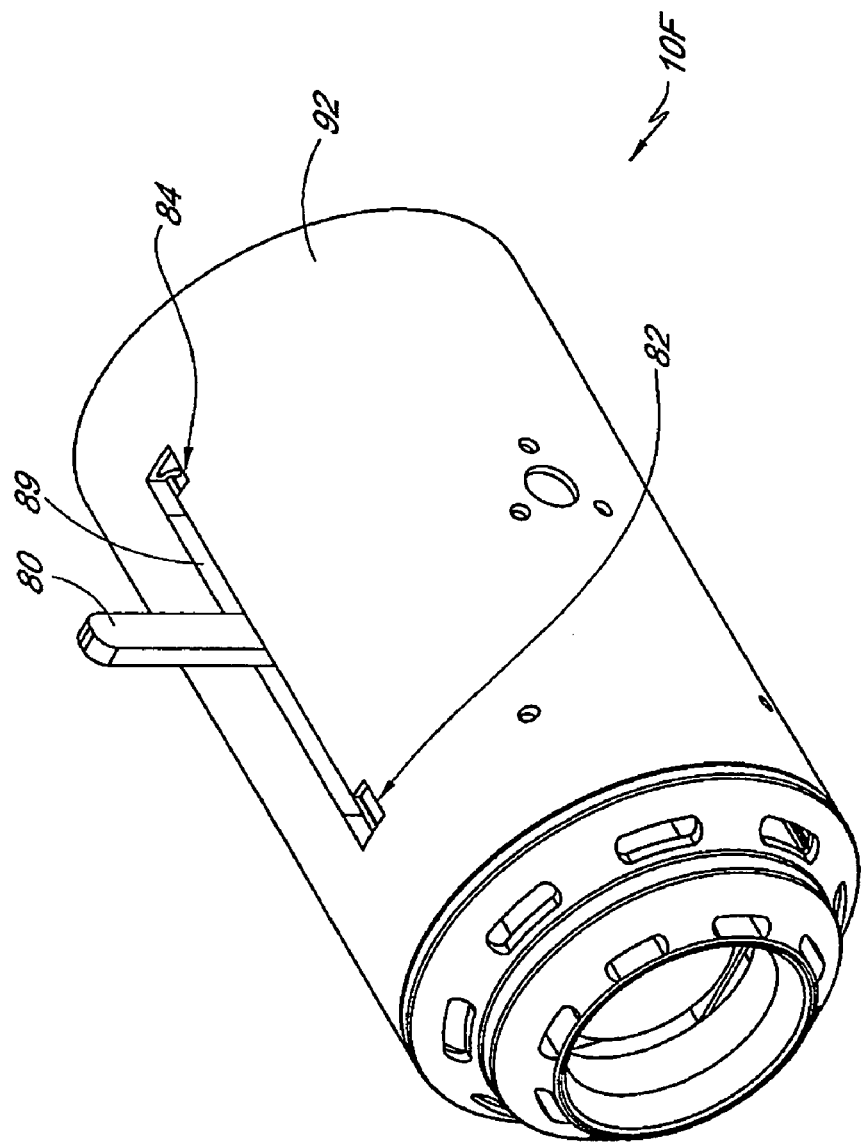
FIGS. 15A and 15B illustrate perspective views of an exemplary keeper-shield assembly.
Figure 15B:
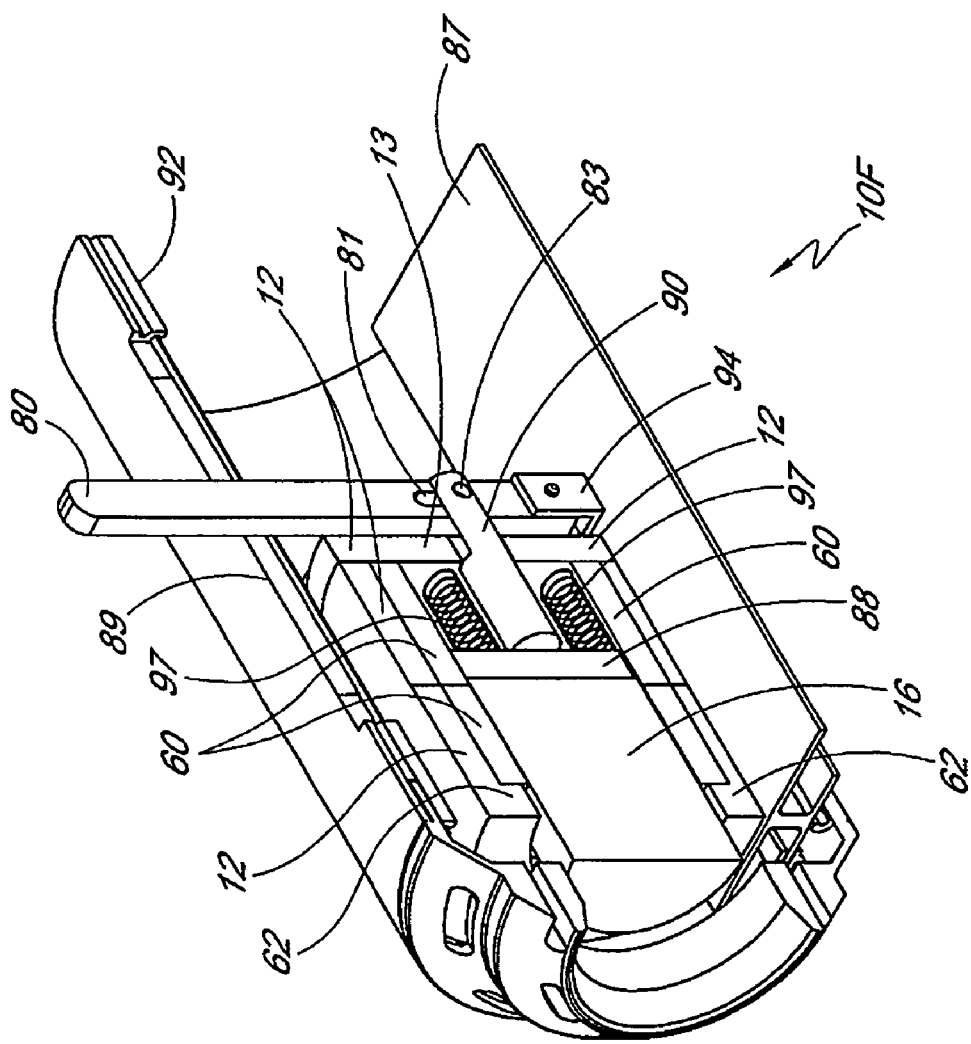

FIGS. 15A is a perspective view and 15B is a partial perspective view of a keeper-shield assembly 10F including a housing 92 configured to support the core 60 and magnet 16. In the embodiment of FIGS. 15A and 15B, extending through a slot 89 in the housing 92 is a lever 80 configured to move the magnet 16 between extended and retracted positions.

In the embodiment illustrated in FIG. 15A, the housing 92 may be made of any material that is durable enough to support the keeper-shield assembly 10F. In one embodiment, the housing 92 comprises aluminum. Extending from the housing 92 is the lever 80, which is mechanically connected to move the magnet 16 between the extended and retracted positions. The housing 92 comprises a fully extended position detent 84 and a fully retracted position detent 82. Detents 82 and 84 are configured to lock the lever 80 into position so that the magnet 16 is locked in either the fully extended or retracted positions, respectively. The magnet 16 may also be moved and maintained in any position in between the extended and retracted positions, such as in the illustration of FIG. 15A. For example, a locking means may be implemented to hold the magnet 16 in a position between the extended and retracted positions. For example, a locking nut may be configured to stabilize the lever 80 against the housing. In one embodiment, a locking nut has sufficient strength to resist the approximately 10 lbs of shear stress exerted by the attraction of the magnet 16 to the back of the keeper-shield assembly 10F.

FIG. 15B is a perspective view of the keeper-shield assembly 10F, where the housing 92 is partially cut away so the keeper-shield assembly 10F and lever mechanism is visible. The lever 80 is mechanically connected to a rod 90 which pushes and pulls the magnet 16 out of and in to the housing 92. The lever 80 is connected to a mount 94 on the housing 92 so that the connection of the lever 80 at the mount 94 is the pivot point for the lever 80. In the embodiment of FIG. 15B, the lever 80 includes a slot 81 through which a connecting pin 83, such as a nut and bolt, is placed. The connecting pin 83 also connects to the rod 90 so that when the lever 80 is moved the adjacent edge of the slot 81 applies pressure to the connecting pin 83, which is then transferred to the rod 90, thereby causing the rod 90 to move. The rod 90 may be mechanically connected to the magnet 16 via physical coupling, such as adhesive bonding, welding, fusing, bolting, threadedly engaging, or other attachment means known to those skilled in the art. In the embodiment of FIG. 15B, an aluminum disk 88 is in physical contact with the magnet 16 and the rod 90 so as to physically couple the magnet 16 to the rod 90. Due to the mechanical contact of the rod 90 and the magnet 16, when the rod 90 is extended the magnet 16 is correspondingly extended.

In general, any type of lever arranged in any configuration within the keeper-shield assembly may be used to apply a force to the magnet 16 pushing the magnet 16 towards the extended position. In an advantageous embodiment, the lever applies a force that is close to the center of the contacting surface of the magnet in order to reduce binding of the magnet along the sides of the keeper 12. In one embodiment, lubrication, or the use of teflon, nylon, or similar material as the non-magnetic core allows a tighter fitting assembly, and gives more flexibility for the point from which the magnet must be pushed out.

With further reference to FIG. 15B, the springs 97 function to aid the movement of the magnet 16 towards an extended position. More particularly, when the magnet 16 is moved towards a retracted position the springs 97 are compressed between the aluminum disk 88 and a radially extending portion 13 of the keeper-shield 12. Thus, the springs 13 exert a force on the aluminum disk 88 and the magnet 16, pushing the magnet 16 towards the extended position. In this way, the springs 13 reduce the force that is required from the rod 90 (via the lever 80) in order to move the magnet 16 towards the extended position.

FIGS. 16A and 16B illustrates perspective views of a keeper-shield assembly 10G. Extending from the housing 92 is the lever 80 configured to move the magnet 16 between the extended and retracted positions.

In the embodiment of FIG. 16A, the housing 92 includes a slot 85 from which extends the lever 80. The slot 85 includes extended position detent 82 and retracted position detent 84. The detents 82 and 84 are configured to lock the lever 80 into position so that the magnet 16 is locked in either the fully extended or retracted positions, respectively. The magnet 16 may also be moved and maintained in any position in between the extended and retracted positions. For example, FIG. 16A illustrates possible positions of the lever 80 using representations of the lever illustrated with broken lines. In particular, when the lever 80 is in the position of lever 80A, the magnet 16 is an intermediate position, between the retracted and extended positions. Similarly, when the lever 80 is in the position of lever 80B, the magnet 16 is the extended position.

FIG. 16B is a perspective view of the housing 92 and keeper-shield assembly 10G illustrated in FIG. 16A, where the housing 92 is partially cut away so the keeper-shield assembly 10G and lever mechanism is visible. In the embodiment illustrated in FIG. 16B, the lever 80 is in the extended position detent 82. A pivot rod 96 is attached to the housing 92 and the lever 80 is attached to the pivot rod 96 so that movement of the lever 80 will pivot around the pivot rod 96. In the embodiment of FIG. 16B, the connecting pin 83 passes through a slot 85 in the lever 80 and also connects to the rod 90 so that when the lever 80 is moved around the pivot point provided by the attachment to the pivot rod 96, the slot 85 applies pressure to the connecting pin 83 and causes the rod 90 to move. Due to the mechanical contact of the rod 90 with the magnet 16, when the rod 90 is extended the magnet 16 is correspondingly extended.

In one embodiment, springs 97 are also used to aid in the extension of the magnet 16 from the keeper-shield assembly 10G. Because the magnetic attraction of the magnet 16 for the back of the keeper-shield assembly 10G pulls the magnet 16 back in when the lever is moved to extend the magnet, the use of springs 97, in addition to the lever, may advantageously reduce the force necessary by the user moving the lever 80 in order to extend the magnet 16. Thus, in one embodiment, springs 97 are chosen to counteract the attraction of the magnet 16 for the keeper-shield assembly 10G. In an exemplary embodiment, short springs with high spring constants are coupled with longer springs with lower spring constants to move the magnet 16 without completely overcoming the attraction of the magnet 16 for the keeper-shield assembly 10G. In this way, when the magnet 16 is in the fully retracted position, a short spring assists extension for the first few centimeters. When that short spring is fully extended, the attractive force between the magnet 16 and the keeper-shield assembly 10G is reduced, but may still represent a challenge to the user moving the lever 80. Accordingly, in one embodiment, longer springs with smaller constants may additionally provide a continued force extending the magnet 16 after the short springs are fully extended. Short springs, long springs, or any combination of springs of continuous length and spring constant may be configured to reduce the force required by the lever 80 to about 5 to 40 lbs. throughout the travel of the lever 80. In an exemplary embodiment, the user contributes about 10 lbs of force to initiate movement of the magnet 16. In order to allow the magnet 16 to be moved with only about 10 lbs of force from the user, springs are selected so that the magnet 16 is not retracted so far into the keeper-shield assembly 10G that excessive force is required to extend the magnet 16 from the keeper-shield assembly 10G.

FIG. 16B also illustrates possible positions of the lever 80 using representations of the lever illustrated with broken lines. In particular, when the lever 80 is in the position of lever 80A, the magnet 16 is an intermediate position, between the retracted and extended positions. Likewise, when the lever 80 is in the position of lever 80C, the magnet 16 is in the retracted position.

Figure 17A:
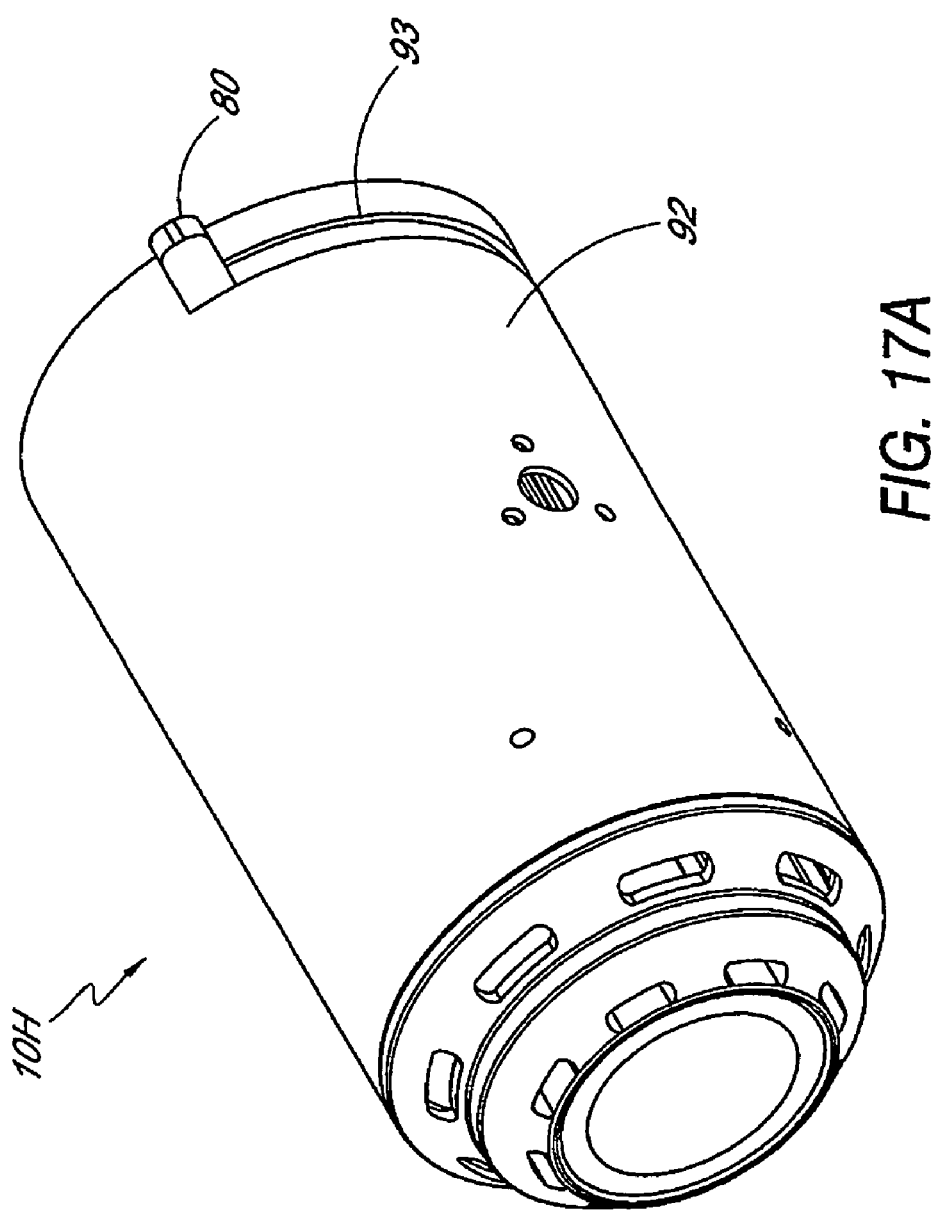
FIGS. 17A and 17B illustrate perspective views of another exemplary keeper-shield assembly.
Figure 17B:
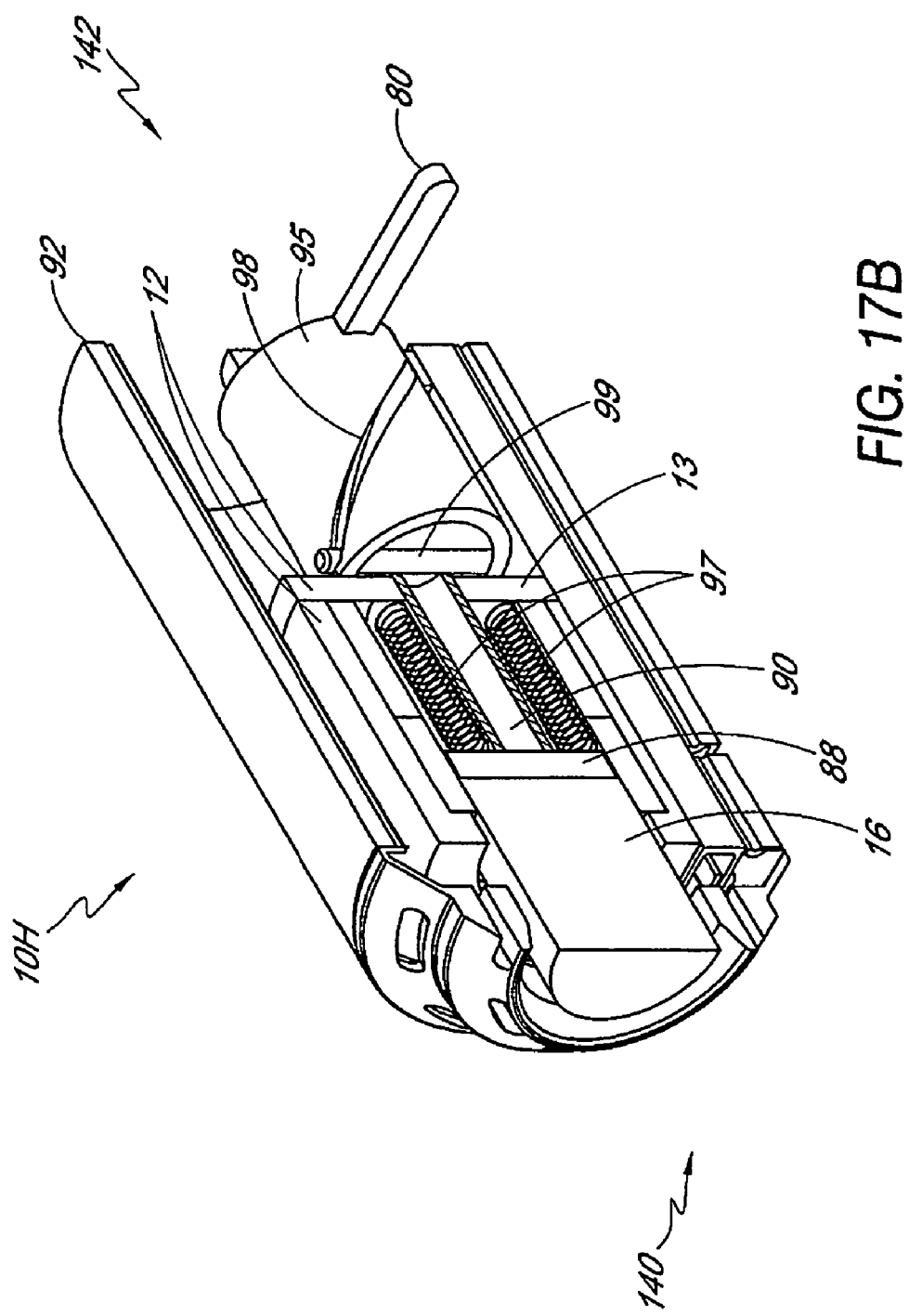

FIGS. 17A and 17B illustrates perspective views of another an exemplary keeper-shield assembly 10H.

In the embodiment of FIG. 17A, the housing 92 includes a slot 93 from which extends the lever 80. The lever 80 is configured to move the magnet 16 between the extended and retracted positions. Although not shown in FIG. 17, the slot 93 may also include detents which are configured to lock the lever into position so that the magnet 16 is locked in either the fully extended or retracted positions. In the embodiment of FIG. 17, the magnet 16 may be moved and maintained in any position in between the extended and retracted positions by moving the lever 80 to different positions in the slot 93. In FIG. 17A the lever 80 is illustrated in the extended positions. Accordingly, the magnet 16 is in the fully extended position. When the lever 80 is moved to the opposite side of the slot 93, the magnet 16 will be in the fully retracted position.

FIG. 17B is a perspective view of the keeper-shield assembly 10H illustrated in FIG. 17A, where the housing 92 is partially cut away so the keeper-shield assembly 10H and lever mechanism is visible. The lever mechanism in the embodiment illustrated in FIG. 17B includes springs 97, a member 99, and rod 90. The lever mechanism further comprises a slotted cylinder 95 that is integrally connected to the lever 80. The slotted cylinder 95 comprises a slot 98 and is configured to rotate within the housing 92 in response to movement of the lever 80. The member 99 extends through the slot 98 of the cylinder 95 so that when the cylinder 95 is rotated the member 99 moves longitudinally through the housing 92. As the member 99 is moved towards a front side 140 of the keeper-shield assembly 10, the rod 90 is pushed towards a front side 140 of the keeper-shield assembly 10H. Thus, the rod 90 pushes the magnet 16 towards an extended position. Similarly, when the member 99 is moved towards a rear side 142 of the keeper-shield assembly 10H, the rod 90 is allowed to move towards the rear side 142. In one embodiment, when the member 99 is moved towards the rear side 142, the rod 90 is pushed towards the rear side 142 due to the movement of the magnet 16 towards a retracted position. In the illustration of FIG. 17B, the lever 80 is in the extended position such that member 99 is at the far range of movement and the magnet 16 is in the fully extended position. The magnet 16 may be moved towards the retracted position by moving the lever 80 upwards in the slot 93 in the housing (FIG. 17A).

With further reference to FIG. 17B, the springs 97 function to aid the movement of the magnet 16 towards an extended position. More particularly, when the magnet 16 is moved towards a retracted position the springs 97 are compressed between the aluminum disk 88 and a radially extending portion 13 of the keeper-shield 12. Thus, the springs 13 exert a force on the aluminum disk 88 and the magnet 16, pushing the magnet 16 towards the extended position. In this way, the springs 13 reduce the force that is required from the rod 90 (via the lever 80, cylinder 95, and member 99) in order to move the magnet 16 towards the extended position.

FIGS. 18A, 18B, 18C, and 18D are selected views of another exemplary embodiment of a keeper-shield assembly. FIG. 18A is an exploded perspective view of a portion of a keeper-shield assembly 101. As illustrated in FIG. 18A, the keeper-shield assembly 101 includes a keeper-shield 12 having a cavity configured to house a core 60. The keeper-shield 12 advantageously comprises a material that is substantially permeable to magnetic flux and the core 60 comprises a non-magnetic material.

In the embodiment illustrated in FIG. 18A, a base 120 is coupled to the keeper-shield 12. In one embodiment, the base 120 is attached to the keeper-shield 12 using one or more threaded bolts that are inserted through holes in the base 120 and tightened into threaded holes in keeper-shield 101. However, the attachment of the base 120 to the keeper-shield 12 may be accomplished using any other attachment means. A base plate 122 is attached to the base 120 with connectors 125 so that the base plate 122 is parallel to the base 120 and a predetermined distance from the base 120. The rod 90 contacts a spacer 130, which in turn contacts the magnet, in order to provide a force against the magnet 16 to aid in moving the magnet 16 towards an extended position. The rod 90 may be coupled to various level mechanisms, as described above in FIGS. 15–17, for example, in order to move the rod 90 within the keeper-shield assembly 10. The rod 90 of FIG. 18A extends through a bushing 138, the base 120, the core 60, and the keeper-shield 12 before contacting the spacer 130.

In the embodiment of FIGS. 18A–18D, one or more cylinders, or cans 124, are fitted into cavities in the base 120. The end of the cans 124 opposite the base 120 are flush with the base plate 122. The base plate 122 includes guide holes 123, each having a diameter smaller than a diameter of the cans, that are centered over each of the cans 124. In one embodiment, each of the cans 124 has an inner cavity that is sufficiently large to house a spring 126. As described above, springs are selected so that the magnet 16 may be retracted into the keeper-shield assembly 101 (providing attenuation of the magnetic field), but not so far retracted that excessive force is required to extend the magnet 16 from the keeper-shield assembly 10. In the embodiment of FIGS. 18A–18D, each of the springs 126 contacts the base plate 122 and is compressed within the cans 124 as the magnet 16 is moved within the core 60. In one embodiment, guide pins 128 extend through a center radius of each spring 126 and through guide holes 123. The guide pins 128, extending through a radius of each spring 126, guide the springs 126 to uniformly compress, thereby maintaining the force contributed by the springs 126 from cycle to cycle. The guide pins 128 are connected to a spacer 130 that is attached to the magnet 16 and, therefore, move as the magnet 16 is moved. Thus, when the magnet 16 is moved into the retracted position, the guide pins 128 may extend outside of the guide holes 123.

In the embodiment of FIG. 18A, an end 132 of the magnet 16 is provided with a label 136 providing information identifying the manufacturer of the keeper-shield assembly 101 and/or other information regarding the specifications of the particular keeper-shield assembly 101. The end 132 may be the north pole of the magnet 16 or the south pole of the magnet 16, depending on the particular application in which the keeper-shield assembly 101 is intended for use. When assembled, the end 132 of the magnet 16 extends into a cap 134 which is coupled to the keeper-shield 12 (See FIG. 18D, for example).

FIG. 18B is a side view of the keeper-shield assembly 101. As shown in FIG. 18B, the cans 124 contact the base plate 122. Accordingly, the springs 126, inside the cans 124, are compressed against the base plate 122 in order to generate an elastic force pushing against the spacer 130 and the magnet 16. In the embodiment of FIG. 18B, the magnet 16 is in a retracted position such that a guide pin 128 extends out of a guide hole 123 in the base plate 122.

FIG. 18C is rear plan view of the keeper-shield assembly 101. As shown in FIG. 18C, connectors 125, such as threaded bolts are used to connect the base plate 122 to the base 120. The base plate 122 is attached so that the base 120 is parallel to, and a predetermined distance from, the base plate 122. The guide holes 123 are sized so that the guide pins 128 may extend through the guide holes 123 while the springs 126 are compressed against the base plate 122.

FIG. 18D is a cross-sectional side view across section A—A of FIG. 18C. As illustrated in FIG. 18D, guide pins 128 extend from the cans 124. The guide pins 128 extend through a central radius of the springs 126 and are attached to the spacer 130. As the magnet 16 is moved to the retracted position, the spring 126 compresses against the base plate 122. Similarly, as the magnet 16 is moved to the extended position, the springs 126 contribute a force on the spacer 130, thus aiding in movement of the magnet towards the extended position.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A keeper-shield assembly for housing a magnet, said keeper-shield assembly comprising:
   a keeper-shield having a central axis and comprising a material substantially permeable to a magnet flux;
   a first cavity in said keeper-shield, said cavity comprising an inner side wail and a base, and said cavity being adapted to accept a core;
   a core located within said cavity and lining at least part of said inner side wall of said cavity, said core having a second cavity adapted to retractably receive a magnet;
   a magnet comprising a front and a rear face, said magnet slidably mounted in said second cavity;
   a lip at an open end of said keeper-shield, said lip extending from an inner side wall of said keeper-shield toward said central axis of said keeper-shield;
   one or more resilient members configured to contribute a force against said magnet; and a movable actuator extending through said base and configured to contribute a force against said magnet, wherein said movable actuator and said one or more resilient members cooperate to move a portion of said magnet from said retracted position to a position outside of said inner cavity; and wherein said keeper-shield is sufficiently thick so that a magnetic flux density is less than about 100 gauss at a distance of about 2 centimeters from said keeper-shield when said magnet is in a retracted position.

2. The keeper-shield assembly of claim 1, wherein said magnet comprises material selected from the group consisting of rare earth elements, ceramics, ceramic oxides, ferrites, and garnets.

3. The magnet keeper-shield assembly of claim 2, wherein said magnet comprises material selected from the group consisting of NdFeB, AlNiCo, and SmCo.

4. The keeper-shield assembly of claim 3, wherein said magnet comprises NdFeB.

5. The keeper-shield assembly of claim 1, wherein said keeper-shield assembly further comprises a spacer of comprising a non-magnetic material at said rear face of said magnet and said movable actuator contacts said spacer.

6. The keeper-shield assembly of claim 1, wherein said lip comprises a magnetically permeable material.

7. The keeper-shield assembly of claim 1, wherein said keeper-shield is configured so that that said magnetic flux density that emanates from said keeper-shield is reduced by at least 10-fold when said magnet is moved from an extended position, wherein said magnet extends out of said second cavity to a retracted position so that said magnet is substantially within said second cavity.

8. The keeper-shield assembly of claim 5, wherein said keeper-shield is configured so that that said magnetic flux density that emanates from said keeper-shield is reduced by at least 50-fold when said magnet is moved from an extended position, wherein said magnet extends out of said second cavity to a retracted position so that said magnet is substantially within said second cavity.

9. The keeper-shield assembly of claim 1, wherein said one or more resilient members comprises springs of varying lengths.

10. The keeper-shield assembly of claim 9, wherein at least one of said springs is coaxial with said movable actuator and is in contact with said rear face of said magnet and said base of said keeper-shield.

11. The keeper-shield assembly of claim 1, wherein said one or more resilient members are springs which extend through said base of said keeper-shield and are in contact with said rear face of said magnet.

12. The keeper-shield assembly of claim 11, further comprising a guide pin coaxially mounted within one or more of each of said one or more springs.

13. The keeper-shield assembly of claim 1, wherein said keeper-shield assembly further comprises a spacer comprising a non-magnetic material and said movable actuator contacts said spacer.

14. The keeper-shield assembly of claim 1, further comprising a housing encasing said keeper-shield, said core, said magnet, said one or more resilient members and said movable actuator, wherein said housing comprises a slot through which a lever moves.

15. The keeper-shield assembly of claim 14, further comprising a lever extending through said slot in said housing and configured to exert a force against said movable actuator.

16. The keeper-shield assembly of claim 15, wherein said lever is moveable in two directions such that when said lever is moved in a first direction said magnet is progressively moved out of said second cavity and when said lever is moved in a second direction said magnet is progressively moved in to said second cavity.

17. The keeper-shield assembly of claim 15, wherein said lever is configured to move said magnet from an extended position wherein a portion of said magnet extends from said first cavity and a retracted position wherein said magnet is within said first cavity.

18. The keeper-shield assembly of claim 14, wherein said lever is moveable by human hands without the aid of additional tools.

19. The keeper-shield assembly of claim 18, wherein a force applied to said lever by human hands to move said lever is less than about 40 pounds.

20. The keeper-shield assembly of claim 18, wherein a force applied to said lever by human hands to move said lever is less than about 20 pounds.

21. The keeper-shield assembly of claim 18 wherein a force applied to said lever by human hands to move said lever is less than about 10 pounds.

22. The keeper-shield assembly of claim 14, further comprising:
    an actuator rod with a first and second end, wherein with said first end is in contact with said magnet;
    a rod located substantially perpendicular to said central axis and coupled to said second end of said actuator rod,
    a cylinder located within said housing and having a spiral slot winding around a portion of said central axis, said spiral slot being configured to slidingly engage said rod, and a lever coupled to said cylinder and configured to translate said actuator rod through said slot in response to rotation of said lever around a portion of said axis.

23. The keeper-shield assembly of claim 22, wherein rotating said lever results in a force being applied to said rod parallel to said central axis.

24. The keeper-shield assembly of claim 22, wherein said cylinder is coaxial with said central axis.

25. The keeper-shield assembly of claim 22, wherein said keeper-shield assembly further comprises a non-magnetic spacer that is in contact with said first end of said actuator rod.

26. The keeper-shield assembly of claim 22, wherein said translation of said rod extends or retracts said magnet relative to said keeper-shield.

27. A keeper-shield assembly comprising:
    a central axis;
    a plurality of keeper-shields each comprising a material substantially permeable to a magnet flux;
    a first cavity in each of said keeper-shields, said first cavity in each of said keeper-shields comprising an inner side wall and a base, and said first cavity in each of said keeper-shields being adapted to accept a core that lines part or all of said inner side wall of said first cavity in each of said keeper-shields; each of said cores having a second cavity adapted to accept either a keeper-shield or a magnet;
    a magnet comprising a front end a rear face, wherein said magnet is slidably mounted in an innermost one of said second cavities;
    at least one resilient member configured to contribute a force against said rear face of said magnet;
    an actuator extending through said base and configured to contribute a force against said rear face of said magnet, wherein a force from said actuator combined with a force from said resilient members moves said magnet from said retracted position to a position wherein a portion of said magnet extends outside of each of said second cavities; and wherein said keeper-shield is sufficiently thick so that a magnetic flux density is less than about 100 gauss at a distance of about 2 centimeters from said keeper-shield assembly when said magnet is in a retracted position.

28. The keeper-shield assembly of claim 27, further comprising a lip at an open end of said keeper-shields, said lip extending from an inner side wall of said keeper-shield toward said central axis of said keeper-shield assembly.

29. The keeper-shield assembly of claim 27, wherein one or more of said keeper-shields comprises a lip at an open end of said plurality of keeper-shields, said lip extending from said inner side wall of at least one of said plurality of keeper-shields toward said central axis of said keeper-shield assembly, and wherein said lip comprises a material such that said magnetic field emanating from said magnet is attenuated by said lip.

30. The keeper-shield assembly of claim 27, wherein said lip is composed of a magnetically permeable material.

31. The keeper-shield assembly of claim 27, wherein one or more of said plurality of keeper-shields is configured so that that said magnetic flux density emanated from said keeper-shield assembly is reduced by at least 10-fold when said magnet is moved from an extended position wherein said magnet extends out of said second cavity to a retracted position wherein said magnet is substantially within said second cavity.

32. The keeper-shield assembly of claim 27, wherein one or more of said keeper-shields are configured so that that said magnetic flux density emanated from said keeper-shield is reduced by at least 50-fold when said magnet is moved from an extended position wherein said magnet extends out of said second cavities to a retracted position wherein said magnet is substantially within said second cavities.

33. A method of delivering magnetic particles to a patient comprising:
   administering a composition to a patient, said composition comprising magnetic particles;
   extending a magnet from a keeper-shield to produce a substantially unattenuated magnetic field at a distance of about 2 cm from front face of the keeper-shield;
   positioning said magnet over a desired location on the patient; and
   at some time following said administering, retracting said magnet into the keeper-shield to produce at least about 10 fold attenuation of the magnetic field at a distance of about 2 cm from the north pole of the magnet, and
   directing said particles to a desired location in the patient with the use of a magnetic field provided by said magnet.

34. The method of claim 33, wherein extending the magnet comprises moving a lever configured to exert a force against the magnet, wherein the force against the magnet moves the permanent magnet in the keeper-shield, and wherein the lever is configured to move the magnet in two opposite directions.

35. An apparatus for directing magnetic particles administered to a patient to a desired location in a patient with the use of a magnetic field comprising:
   means for extending a magnet from a keeper-shield assembly to produce a substantially unattenuated magnetic field at a distance of about 2 cm from a north pole of the magnet;
   means for positioning said magnet over a desired location on the patient; and
   means for retracting said magnet into the keeper-shield to produce at least about 10 fold attenuation of the magnetic field at a distance of about 2 cm from the north pole of the magnet.

* * * * *